(12) United States Patent
Gelfand et al.

(10) Patent No.: US 8,007,460 B2
(45) Date of Patent: *Aug. 30, 2011

(54) PATIENT HYDRATION SYSTEM AND METHOD

(75) Inventors: Mark Gelfand, New York, NY (US); Howard R. Levin, Teaneck, NJ (US)

(73) Assignee: PLC Medical Systems, Inc., Franklin, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/800,699

(22) Filed: May 20, 2010

(65) Prior Publication Data

US 2010/0280445 A1 Nov. 4, 2010

Related U.S. Application Data

(63) Continuation of application No. 11/408,851, filed on Apr. 21, 2006, now Pat. No. 7,758,562, which is a continuation-in-part of application No. 10/936,945, filed on Sep. 9, 2004, now Pat. No. 7,938,817.

(51) Int. Cl.
*A61M 31/00* (2006.01)
*A61M 1/00* (2006.01)
(52) U.S. Cl. .............................. 604/67; 604/503; 604/31
(58) Field of Classification Search ................ 604/65–7, 604/30, 31, 503, 506, 508, 517, 245
See application file for complete search history.

(56) References Cited

U.S. PATENT DOCUMENTS

| | | | |
|---|---|---|---|
| 3,954,010 A | 5/1976 | Hilblom | |
| 4,132,644 A | 1/1979 | Kolberg | |
| 4,146,029 A | 3/1979 | Ellinwood, Jr. | |
| 4,204,957 A | 5/1980 | Weickhardt | |
| 4,216,462 A | 8/1980 | McGrath et al. | |
| 4,229,299 A | 10/1980 | Savitz et al. | |
| 4,261,360 A | 4/1981 | Perez | |
| 4,275,726 A | 6/1981 | Schael | |
| 4,291,692 A | 9/1981 | Bowman et al. | |
| 4,343,316 A | 8/1982 | Jespersen | |

(Continued)

FOREIGN PATENT DOCUMENTS

EP 0258690 3/1988

(Continued)

OTHER PUBLICATIONS

Written Opinion of the International Searching Authority for PCT Application No. PCT/US2007/009683 mailed Nov. 24, 2008, 8 pgs. (unnumbered).

(Continued)

*Primary Examiner* — Kevin C Sirmons
*Assistant Examiner* — Laura C Schell
(74) *Attorney, Agent, or Firm* — Iandiorio Teska & Coleman

(57) ABSTRACT

A patient hydration system including an infusion device for administering hydration fluid to a patient, and a hydration fluid measurement device responsive to a source of hydration fluid, a patient urine output measurement device. A controller is responsive to the hydration fluid measurement device and the patient urine output measurement device. The controller operates the infusion device, in response to the patient urine output measurement device and the hydration fluid measurement device, to hydrate the patient based on the patient's urine output. The controller also monitors the operation history of the infusion device thereby providing redundancy in the measurement of the amount of hydration fluid administered to the patient.

22 Claims, 15 Drawing Sheets

U.S. PATENT DOCUMENTS

| | | | |
|---|---|---|---|
| 4,448,207 A | 5/1984 | Parrish | |
| 4,449,538 A | 5/1984 | Corbitt et al. | |
| 4,504,263 A | 3/1985 | Steuer et al. | |
| 4,658,834 A | 4/1987 | Blankenship et al. | |
| 4,712,567 A | 12/1987 | Gille et al. | |
| 4,718,576 A * | 1/1988 | Tamura et al. | 222/63 |
| 4,728,433 A | 3/1988 | Buck et al. | |
| 4,813,925 A | 3/1989 | Anderson, Jr. et al. | |
| 4,923,598 A | 5/1990 | Schal | |
| 4,994,026 A | 2/1991 | Fecondini | |
| 5,098,379 A | 3/1992 | Conway et al. | |
| 5,176,148 A | 1/1993 | Wiest et al. | |
| 5,207,642 A | 5/1993 | Orkin et al. | |
| 5,722,947 A | 3/1998 | Jeppsson et al. | |
| 5,769,087 A | 6/1998 | Westphal et al. | |
| 5,814,009 A | 9/1998 | Wheatman | |
| 5,891,051 A | 4/1999 | Han et al. | |
| 5,910,252 A | 6/1999 | Truitt et al. | |
| 5,916,153 A | 6/1999 | Rhea, Jr. | |
| 5,916,195 A | 6/1999 | Eshel et al. | |
| 5,981,051 A | 11/1999 | Motegi et al. | |
| 6,010,454 A | 1/2000 | Arieff et al. | |
| 6,171,253 B1 | 1/2001 | Bullister et al. | |
| 6,231,551 B1 | 5/2001 | Barbut | |
| 6,272,930 B1 | 8/2001 | Crozafon et al. | |
| 6,514,226 B1 | 2/2003 | Levin et al. | |
| 6,531,551 B2 | 3/2003 | Levin et al. | |
| 6,537,244 B2 | 3/2003 | Paukovits et al. | |
| 6,554,791 B1 | 4/2003 | Cartledge et al. | |
| 6,640,649 B1 | 11/2003 | Paz et al. | |
| 6,740,072 B2 | 5/2004 | Starkweather et al. | |
| 6,752,779 B2 | 6/2004 | Paukovits et al. | |
| 6,796,960 B2 | 9/2004 | Cioanta et al. | |
| 6,827,702 B2 | 12/2004 | Lebel et al. | |
| 6,942,637 B2 | 9/2005 | Cartledge et al. | |
| 7,029,456 B2 | 4/2006 | Ware et al. | |
| 7,044,002 B2 | 5/2006 | Ericson et al. | |
| 7,137,964 B2 | 11/2006 | Flaherty | |
| 7,278,983 B2 | 10/2007 | Ireland et al. | |
| 2002/0025597 A1 | 2/2002 | Matsuda | |
| 2002/0072647 A1 | 6/2002 | Shock et al. | |
| 2002/0107536 A1 | 8/2002 | Hussein | |
| 2002/0151834 A1 | 10/2002 | Utterberg | |
| 2002/0161314 A1 | 10/2002 | Sarajarvi | |
| 2003/0048185 A1 | 3/2003 | Citrebaum et al. | |
| 2003/0048432 A1 | 3/2003 | Jeng et al. | |
| 2003/0114786 A1 | 6/2003 | Hiller et al. | |
| 2004/0025597 A1 | 2/2004 | Ericson et al. | |
| 2004/0059295 A1 | 3/2004 | Cartledge et al. | |
| 2004/0081585 A1 | 4/2004 | Reid | |
| 2004/0087894 A1 | 5/2004 | Flaherty | |
| 2004/0122353 A1 | 6/2004 | Shahmirian et al. | |
| 2004/0133187 A1 | 7/2004 | Hickle | |
| 2004/0163655 A1 | 8/2004 | Gelfand et al. | |
| 2004/0167415 A1 | 8/2004 | Gelfand et al. | |
| 2004/0167464 A1 | 8/2004 | Ireland et al. | |
| 2004/0176703 A1 | 9/2004 | Christensen et al. | |
| 2004/0193328 A1 | 9/2004 | Zaitsu et al. | |
| 2004/0243075 A1 | 12/2004 | Harvie | |
| 2005/0027254 A1 | 2/2005 | Vasko | |
| 2005/0065464 A1 | 3/2005 | Talbot et al. | |
| 2005/0085760 A1 | 4/2005 | Ware et al. | |
| 2006/0052764 A1 | 3/2006 | Gelfand et al. | |
| 2006/0064053 A1 | 3/2006 | Bollish et al. | |
| 2006/0184084 A1* | 8/2006 | Ware et al. | 604/5.01 |
| 2006/0235353 A1 | 10/2006 | Gelfand et al. | |
| 2006/0253064 A1 | 11/2006 | Gelfand et al. | |
| 2006/0270971 A1 | 11/2006 | Gelfand et al. | |
| 2007/0088333 A1 | 4/2007 | Levin et al. | |
| 2008/0027409 A1 | 1/2008 | Rudko et al. | |
| 2008/0033394 A1 | 2/2008 | Gelfand et al. | |
| 2008/0171966 A1 | 7/2008 | Rudko et al. | |
| 2008/0221512 A1 | 9/2008 | Da Silva et al. | |

FOREIGN PATENT DOCUMENTS

| | | |
|---|---|---|
| WO | WO 99/06087 A1 | 2/1999 |
| WO | WO 2006/041496 A1 | 4/2006 |

OTHER PUBLICATIONS

Written Opinion of the International Searching Authority for PCT Application No. PCT/US07/09685 mailed Jul. 18, 2008, 12 pgs. (unnumbered).

Written Opinion of the International Searching Authority for PCT Application No. PCT/US07/09684 mailed Jul. 21, 2008, 9 pgs. (unnumbered).

Written Opinion of the International Searching Authority for PCT Application No. PCT/US08/07845 mailed Sep. 17, 2008, 7 pgs. (unnumbered).

Written Opinion of the International Searching Authority for PCT Application No. PCT/US08/07841 mailed Sep. 18, 2008, 6 pgs. (unnumbered).

Written Opinion of the International Searching Authority for PCT Application No. PCT/US09/02739 mailed Jun. 19, 2009, 6 pgs. (unnumbered).

Written Opinion of the International Searching Authority for PCT Application No. PCT/US2007/021791 mailed May 8, 2008, 9 pgs. (unnumbered).

Written Opinion of the International Searching Authority for PCT Application No. PCT/US05/08948 mailed Oct. 3, 2006, 5 pgs. (unnumbered).

James M. Gloor and Vincente E., *Reflux and Obstructive Nephropathy*, Atlas of Diseases of the Kidney, online edition, vol. Two, Section 1, Ch. 8, pp. 8.1-8.25, 1999.

Lelarge et al., "*Acute Unilateral Renal Failure and Contralateral Ureteral Obstruction*", American Journal of Kidney Diseases, vol. XX, No. 3, Sep. 1992, pp. 286-288.

Doty et al., "Effect of Increased Renal Venous Pressure on Renal Function", Journal of Trauma: Injury, Infection and Critical Care, vol. 47, No. 6, Dec. 1999, pp. 1000-1003.

Edelson et al., "Pharmacokinetics of Iohexol, a New Nonionic Radiocontrast Agent, in Humans", Journal of Pharmaceutical Sciences, vol. 73, No. 7, Jul. 1984, pp. 993-995.

Hvistendahl et al., "Renal Hemodynamic Response to Gradated Ureter Obstruction in the Pig", Nephron 1996; 74, pp. 168-174.

Pedersen et al., "Renal Water and Sodium Handling During Gradated Unilateral Ureter Obstruction", Scand J Urol Nephrol 2002; 36, pp. 163-172.

Brezis et al., "Hypoxia of the Renal Medulla—its Implications for Disease" New England Journal of Medicine, vol. 322, No. 10, Mar. 9, 1995 pp. 647-655.

Heyman et al., "*Pathophysiology of Radiocontrast Nephropathy: A Role for Medullary Hypoxia*", Investigative Radiology, vol. 34, No. 11, Nov. 1999, pp. 685-691.

Urexact ® 2000 System, mhtml:file://C:\Documents%20and%20Settings\bob\Local%20Settings\Temporary%20Int...(3 pages).

Bard Lubricath 3-Way Catheters, http://www.bardmedical.com/urology/cathtour/3way.html (1 page).

Foley Catheter Introduction, Foley Catheter, http://www.emedicinehealth.com/articles/11633-1.asp; http://www.emedicinehealth.com/articles/11633-8.asp (2 pages).

Gambro Acute Renal Failure, Prisma Machine, http://www.gambro.com/Page.asp?id=2446; http://www.gambro.com/upload/press_media_toolkit/download_images/Prisma.jpg (2 pages).

Angiometrix, The Metricath System, http://www.angiometrx.com/Metricath%20System.htm (1 page).

Merit Medical Systems, Inc. 2003 Annual Report; Balloon Inflation Devices & Pressure Monitoring Syringes; Transducers and Accessories, http://www.corporatewindow.com/annuals/mmsi03/10kpage5.html (3 pages).

Cardiovascular Mikro-Tip Pressure Transducer Catheters, http://www.millarinstruments.com/products/cardio/cardio_sngldual.html (5 pages).

Infusion Dynamics The Power Infuser, http://www.infusiondynamics.com/powerinfuser/ (2 pages).

Ultra-Low Profile Single Point Load Cell—S215, http://smdsensors.com/detail_pgs/s215.htm (2 pages).

Rihal et al., *Incidence and Prognostic Importance of Acute Renal Failure After Percutaneous Coronary Int.*

Solomon et al., Effects of Saline, Mannitol, and Furosemide on Acute Decreases in Renal Function Induced by Radiocontrast Agents, The New England Journal of Medicine, vol. 331:1416-1420, Nov. 24, 1994 No. 21 (11 pages).

Wakelkamp et al., *The influence of drug input rate on the development of tolerance to frusemide*, Br. J. Clin. Pharmacol 1998; 46:479-487, pp. 479-487.

Stevens, MD et al., A Prospective Randomized Trial of Prevention Measures in Patients at High Risk for Contrast Nephropathy, Journal of the American College of Cardiology, vol. 33, No. 2, 1999, Feb. 1999, pp. 403-411.

Weinstein et al., "Potential Deleterious Effect of Furosemide in Radiocontrast Nephropathy", Nephron 1992; 62: 413-415.

International Preliminary Report on Patentability, International Application No. PCT/US2007/009683, issued by the International Searching Authority, Dec. 31, 2008, 8 pgs. (unnumbered).

Office Action of the Canadian Intellectual Property Office for Canadian Patent Application No. 2,579,829 mailed Jun. 13, 2008 (two (2) pages).

Rosamilia et al., Electromotive Drug Administration of Lidocaine and Dexamethasone Followed by Cystodistension in Women With Interstitial Cystitis, International Urogynecological Journal Pelvic Floor Dysfunction 1997; 8(3): 142-5.

Written Opinion of the International Searching Authority for PCT Application No. PCT/US2010/000137 mailed, Mar. 16, 2010, 11 pgs. (unnumbered).

\* cited by examiner

PATIENT HYDRATION SYSTEM AND METHOD

RELATED APPLICATIONS

This application is a continuation application of U.S. patent application Ser. No. 11/408,851, filed Apr. 21, 2006 now U.S. Pat. No. 7,758,562 which is a continuation-in-part application of U.S. patent application Ser. No. 10/936,945, filed Sep. 9, 2004 now U.S. Pat. No. 7,938,817. All of the above applications are herein incorporated by reference in their entirety.

SEQUENCE LISTING/COMPUTER PROGRAM LISTING

A computer program listing appendix which is incorporated into this application by reference is submitted on a single compact disc including one (1) file: Name: "Source code.txt"; Size in Bytes: 14 KB; Date of Creation: Jul. 12, 2011.

FIELD OF THE INVENTION

This invention relates to a patient hydration system and method wherein the rate of hydration fluid delivered to the patient is automatically adjusted based on the urine output of the patient to maintain, as necessary, a zero, positive, or negative net fluid balance in the patient.

BACKGROUND OF THE INVENTION

The "cath lab" in a hospital is where a patient is injected with a radiocontrast media, imaged, diagnosed, and often operated on. Typically, a cardiologist refers the patient to the cath lab and the patient is instructed not to eat or drink the night before. In the case of a patient suffering a heart attack, the patient may be transferred directly to the cath lab.

Often, the patient is dehydrated when the patient arrives at the cath lab. The patient is prepped and the radiocontrast media injected. If, after imaging, a possible problem is detected, intervention occurs in the form of angioplasty, the placement of a stent, heart valve repair surgery, and the like. During these procedures, additional radiocontrast media may be injected into the patient and the patient imaged so the cardiac surgeon can view the progress of the operation.

Unfortunately, the radiocontrast media is toxic to the patient especially a patient who is dehydrated at the time the radiocontrast media is injected. A patient who already suffers from various medial problem such as diabetes or kidney problems is even more prone to medial problems due to the injection of the radiocontrast media.

It has been observed that dehydration increases the risk of radiocontrast nephropathy (RCN) when radiocontrast agents are injected into a patient during coronary and peripheral vascular catheterization procedures. RCN is the third most common cause of hospital-acquired renal failure. It occurs in over 5% of patients with any baseline renal insufficiency and in 50% of patients with preexisting chronic renal insufficiency and diabetes. Radiocontrast media has a variety of physiologic effects believed to contribute to the development of RCN. One of the main contributors is renal medullary ischemia, which results from a severe, radiocontrast-induced reduction in renal/intrarenal blood flow and oxygen delivery. The medullary ischemia induces ischemia and/or death of the metabolically active areas of the medulla responsible for urine formation, called the renal tubules. Medullary ischemia is attributed to the increase of oxygen demand by the kidney struggling to remove the radiocontrast media from blood plasma and excrete it from the body at the same time as the normal process of controlling the concentration of urine. Oxygen consumption in the medulla of the kidney is directly related to the work of concentrating urine. Since the presence of radiocontrast media in the urine makes it much more difficult for the kidney to concentrate urine, the work of the medulla outstrips the available oxygen supply and leads to medullary ischemia.

Although the exact mechanisms of RCN remain unknown, it has been consistently observed that patients with high urine output are less vulnerable to contrast injury. It is also clear that dehydration increases the risk of RCN, likely because urine (and contrast media inside the kidney) is excessively concentrated. As a result, patients predisposed to RCN are hydrated via intravenous infusion of normal saline before, during and after the angiographic procedure. Hydration is commonly performed at a conservative rate, especially in patients with existing heart and kidney dysfunction, since over-hydration can result in pulmonary edema (fluid in the lungs), shortness of breath, the need for intubation, and even death. Thus, the patients at highest risk for RCN are those least likely to receive the only proven therapy for preventing RCN (I.V. hydration) due to the unpredictability of side effects from I.V. hydration.

A major limitation to the more widespread use of the already known therapeutic, or optimal, levels of I.V. hydration is the current inability to balance the amount of fluid going into the patient to the amount of fluid being removed or excreted from the patient. It is possible to have a nurse measure a patient's urine output frequently but this method is impractical as nurses are often responsible for the care of many patients. In addition, the only accurate method of measuring urine output is to place a catheter into the patient's urinary bladder. Without a catheter, the patient must excrete the urine that may have been stored in the bladder for several hours. During this time, the amount of I.V. hydration can be significantly less than the amount of urine produced by the kidneys and stored in the bladder, leading to dehydration. Since patients do not normally have such a catheter during procedures using radiocontrast media, a valid measurement of urine output is not possible.

There seems to be indisputable scientific evidence that RCN in patients with even mild baseline renal insufficiency can lead to long term complications and even increased risk of mortality. This scientific knowledge has not yet been extended to daily clinical practice as routine monitoring of renal function post-catheterization is not performed and limits the identification of the known short-term clinical complications.

At the same time, there is a great deal of awareness in clinical practice that patients with serious renal insufficiency (serum creatinine (Cr)≧2.0) often suffer serious and immediate damage from contrast. Many cardiologists go considerable length to protect these patients including slow, overnight hydration (an extra admission day), administration of marginally effective but expensive drugs, or even not performing procedures at all.

There are approximately 1 million inpatient and 2 million outpatient angiography and angioplasty procedures performed in the U.S. per year (based on 2001 data). Based on the largest and most representative published studies of RCN available to us (such as Mayo Clinic PCI registry of 7,586 patients) we believe that 4% of patients have serious renal insufficiency (Cr≧2.0). This results in the initial market potential of 40 to 120 thousand cases per year from interventional cardiology alone. There is also a significant potential contribution from peripheral vascular procedures, CT scans and biventricular pacemaker leads placement. As the awareness of the RCN increases, the market can be expected to increase to 10% or more of all cases involving contrast.

According to the prior art, hydration therapy is given intravenously (I.V.) when someone is losing necessary fluids at a rate faster than they are retaining fluids. By giving the hydration therapy with an I.V., the patient receives the necessary fluids much faster than by drinking them. Also, dehydration can be heightened by hyperemesis (vomiting), therefore the I.V. method eliminates the need to take fluids orally. An anesthetized or sedated patient may not be able to drink. Hydration is used in clinical environments such as surgery, ICU, cathlab, oncology center and many others. At this time, hydration therapy is performed using inflatable pressure bags and/or I.V. pumps. A number of I.V. pumps on the market are designed for rapid infusion of fluids (as opposed to slow I.V. drug delivery) for perioperative hydration during surgery, ICU use and even emergency use for fluid resuscitation.

An infusion pump is a device used in a health care facility to pump fluids into a patient in a controlled manner. The device may use a piston pump, a roller pump, or a peristaltic pump and may be powered electrically or mechanically. The device may also operate using a constant force to propel the fluid through a narrow tube, which determines the flow rate. The device may include means to detect a fault condition, such as air in, or blockage of, the infusion line and to activate an alarm.

An example of a device for rapid infusion of fluids is the Infusion Dynamics (Plymouth Meeting, Pa.) Power Infuser. The Power Infuser uses two alternating syringes as a pumping engine. Since it is only intended to deliver fluids (not medication), the Power Infuser has accuracy of 15%. It provides a convenient way to deliver colloid as well as crystalloid for hydration during the perioperative period among other possible clinical settings. The Power Infuser provides anesthesiologists with the ability to infuse at rates similar to that seen with pressure bags, but with more exact volume control. The maximum infusion rate is 6 l/hr. It has the flexibility of infusing fluid at 0.2, 1, 2, 4 and 6 L/hr. A bolus setting of 250 mL will deliver that volume in 2.5 min. In a large blood loss surgical case, the use of Power Infuser enables large volumes of colloid to be delivered to restore hemodynamics.

It is also known in the art that loop diuretics such as furosemide (frusemide) reduce sodium reabsorption and consequentially reduce oxygen consumption of the kidney. They also reduce concentration of contrast agents in the urine-collecting cavities of the kidney. They induce diuresis (e.g., patient produces large quantities of very dilute urine) and help remove contrast out of the kidney faster. Theoretically, they should be the first line of defense against RCN. In fact, they were used to prevent RCN based on this assumption until clinical evidence suggested that they were actually deleterious. More recently, doubts have been raised regarding the validity of those negative clinical studies.

In two clinical studies by Solomon R., Werner C, Mann D. et al. "Effects of saline, mannitol, and furosemide to prevent acute decreases in renal function induced by radiocontrast agents", N Engl J Med, 1994; 331:1416-1420 and by Weinstein J. M., Heyman S., Brezis M. "Potential deleterious effect of furosemide in radiocontrast nephropathy", Nephron 1992; 62:413-415, as compared with hydration protocol, hydration supplemented with furosemide adversely affected kidney function in high-risk patients given contrast. Weinstein et al. found that furosemide-treated subjects lost 0.7 kg on average, whereas a 1.3-kg weight gain was noted in patients randomized to hydration alone, suggesting that in furosemide-treated subjects the hydration protocol has been insufficient and patients were dehydrated by excessive diuresis.

The clinical problem is simple to understand: diuresis is widely variable and unpredictable but the fluid replacement (hydration) at a constant infusion rate is prescribed in advance. To avoid the risk of pulmonary edema, fluid is typically given conservatively at 1 ml/hr per kg of body weight. The actual effect of diuretic is typically not known for 4 hours (until the sufficient amount of urine is collected and measured) and it is too late and too difficult to correct any imbalance. Meanwhile, patients could be losing fluid at 500 ml/hour while receiving the replacement at only 70 ml/hour. The effects of forced diuresis without balancing are illustrated in the research paper by Wakelkamp et. al. "The Influence of Drug input rate on the development of tolerance to furosemide" Br J Clin. Pharmacol. 1998; 46: 479-487. In that study, diuresis and natriuresis curves were generated by infusing 10 mg of I.V. furosemide over 10 min to human volunteers. From that paper it can be seen that a patient can lose 1,300 ml of urine within 8 hours following the administration of this potent diuretic. Standard unbalanced I.V. hydration at 75 ml/h will only replace 600 ml in 8 hours. As a result the patient can lose "net" 700 ml of body fluid and become dehydrated. If such patient is vulnerable to renal insult, they can suffer kidney damage.

To illustrate the concept further, the effects of diuretic therapy on RCN were recently again investigated in the PRINCE study by Stevens et al. in "A Prospective Randomized Trial of Prevention Measures in Patients at High Risk for Contrast Nephropathy, Results of the PRINCE. Study" JACC Vol. 33, No. 2, 1999 February 1999:403-11. This study demonstrated that the induction of a forced diuresis while attempting to hold the intravascular volume in a constant state with replacement of urinary losses provided a modest protective benefit against contrast-induced renal injury, and importantly, independent of baseline renal function. This is particularly true if mean urine flow rates were above 150 ml/h. Forced diuresis was induced with intravenous crystalloid, furosemide, and mannitol beginning at the start of angiography.

The PRINCE study showed that, in contrast to the Weinstein study, forced diuresis could be beneficial to RCN patients if the intravascular volume was held in a constant state (no dehydration). Unfortunately, there are currently no practical ways of achieving this in a clinical setting since in response to the diuretic infusion the patient's urine output changes rapidly and unpredictably. In the absence of special equipment, it requires a nurse to calculate urine output every 15-30 minutes and re-adjust the I.V. infusion rate accordingly. While this can be achieved in experimental setting, this method is not possible in current clinical practice where nursing time is very limited and one nurse is often responsible for monitoring the care of up to ten patients. In addition, frequent adjustments and measurements of this kind often result in a human error.

Forced hydration and forced diuresis are known art that has been practiced for a long time using a variety of drugs and equipment. There is a clear clinical need for new methods and devices that will make this therapy accurate, simple to use and safe.

SUMMARY OF THE INVENTION

It is therefore an object of this invention to provide a patient hydration system and method.

It is a further object of this invention to provide such a system and method which prevents kidney damage in a patient.

It is a further object of this invention to provide such a system and method which protects the patient undergoing a medical procedure involving a radiocontrast agent from kidney damage.

It is a further object of this invention to provide such a system and method which incorporates a balancing feature intended to prevent dehydration, overhydration, and to maintain a proper intravascular volume.

It is a further object of this invention to provide a balanced diuresis method which automatically balances fluid loss in the urine.

It is a further object of this invention to provide such a system and method which is accurate, easy to implement, and simple to operate.

It is a further object of this invention to provide such a system and method which is particularly useful in the clinical setting of forced diuresis with drugs known as I.V. loop diuretics.

It is a further object of this invention to provide such a system and method in which the amount of hydration fluid injected into the patient is confirmed by a redundant control loop.

The subject invention results from the realization that radiocontrast nephropathy in particular and patient dehydration in general can be prevented by automatically measuring the urine output of the patient and adjusting the rate of delivery of a hydration fluid to the patient to achieve, as necessary, a zero, positive, or negative net fluid balance in the patient. Redundancy and safety is provided by controlling the infusion rate based both on the operation history of the infusion pump and a separate measurement of the fluid pumped out of the source of hydration fluid.

The subject invention, however, in other embodiments, need not achieve all these objectives and the claims hereof should not be limited to structures or methods capable of achieving these objectives.

A patient hydration system in accordance with this invention features an infusion device for administering hydration fluid to a patient. A hydration fluid measurement device is responsive to a source of hydration fluid. There is also a patient urine output measurement device. A controller is responsive to the hydration fluid measurement device and the patient urine output measurement device. The controller controls the operation of the infusion device in response to the patient urine output measurement device and the hydration fluid measurement device, to hydrate the patient based on the patient's urine output. The controller also monitors the operation history of the infusion device thereby providing redundancy in the measurement of the amount of hydration fluid administered to the patient.

In one example, the controller is configured to output an alarm signal if the operation history of the infusion device yields a hydration fluid administration quantity different from the measurement of the hydration fluid by a first predetermined amount. Also, controller can be configured to adjust the operation of the infusion device if the operation history of the infusion device yields a hydration fluid administration quantity different from the measurement of the hydration fluid by second predetermined amount. Typically, the controller is further configured to operate the infusion device at a predetermined maximum infusion rate irrespective of the patient's urine output and to operate the infusion device at a predetermined minimum infusion rate irrespective of the patient's urine output.

In one example, the infusion device is a pump, the hydration fluid measurement device includes a weighing mechanism such as a strain gauge responsive to the source of hydration fluid. The patient urine output measurement device may include a weighing mechanism such as a strain gauge responsive to a reservoir of urine output by the patient.

A method of hydrating a patient in accordance with this invention includes administering hydration fluid to the patient, measuring the patient's urine output, and controlling the amount of hydration fluid administered to the patient based on the patient's urine output and redundantly monitoring the amount of hydration fluid administered to the patient. Typically, the hydration fluid administered to the patient is from a source of hydration fluid and by an infusion device. The operation history of the infusion device is monitored and the source of hydration fluid is also monitored to provide redundancy.

An alarm signal can be generated if the operation history of the infusion device yields a hydration fluid administration quantity different from the monitored source of hydration fluid by a first predetermined amount. Also, the operation of the infusion device can be adjusted if the operation history of the infusion device yields a hydration fluid administration quantity different from the monitored source of hydration fluid by second predetermined amount.

In one example, monitoring the source of hydration fluid includes weighing the source of hydration fluid and measuring the patient's urine output includes weighing the patient's urine output.

One fluid management system for a patient injected with a contrast agent in accordance with this invention features a console for mounting on an IV pole, a first attachment mechanism extending from the console for hanging a urine collection chamber, a first weighing device associated with the console and responsive to the first attachment, a second attachment extending from the console for hanging a source of hydration fluid, and a second weighing device associated with the console and responsive to the second attachment for weighing the source of hydration fluid. An infusion pump is integrated with the console and configured to pump hydration fluid from the source of hydration fluid into the patient. A controller is located in the console and is responsive to the first and second weighing devices. The controller controls the infusion pump to hydrate the patient based on the patient's urine output to prevent radiocontrast nephropathy. The controller monitors the amount of hydration fluid administered to the patient based on the weight of the source of hydration fluid and also monitors the operation of the infusion pump.

One example of a fluid management method for a patient injected with a contrast agent features weighing the patient's urine output, weighing a source of hydration fluid, infusing hydration fluid from the source of hydration fluid into the patient via an infusion pump, controlling the infusion rate to hydrate the patient based on the patient's urine output to prevent radiocontrast nephropathy, monitoring the amount of hydration fluid administered to the patient based on the weight of the source of hydration fluid, and monitoring operation of the infusion pump.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
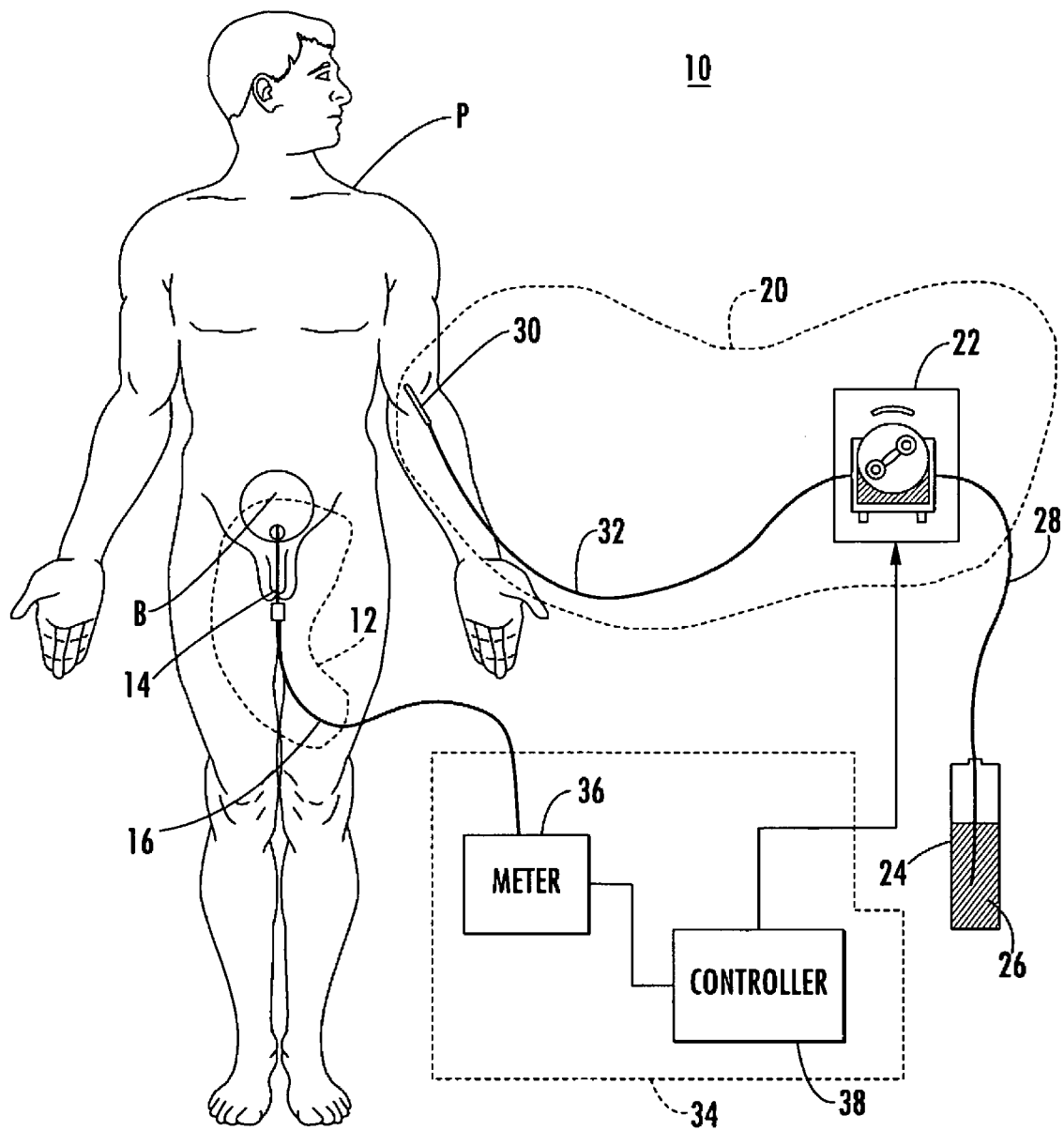
FIG. 1 is a schematic view of an example of a patient hydration system in accordance with the subject invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Patient hydration system 10, FIG. 1 according to this invention includes urine collection system 12 connected to patient P. Infusion system 20 typically includes an infusion device such as infusion pump 22 (e.g., a peristaltic pump) connected to source 24 of infusion fluid 26 (e.g., saline) by tubing 28. I.V. needle 30 is inserted in a vein of patient P and is connected to infusion pump 22 via tubing 32.

A control system or hydration balance means 34 detects the amount of urine output by the patient and automatically adjusts the infusion rate of infusion pump 22 to achieve, as necessary, a zero, positive, or negative net fluid balance in the patient. Typically, urine collection system 12 includes catheter 14 (e.g., a Foley catheter) placed in the bladder B of patient P. Tubing 16 connects catheter 14 to meter 36. Controller 38, typically programmable, is responsive to the output of meter 36 and is configured to adjust the infusion rate of infusion pump 22.

Figure 2:
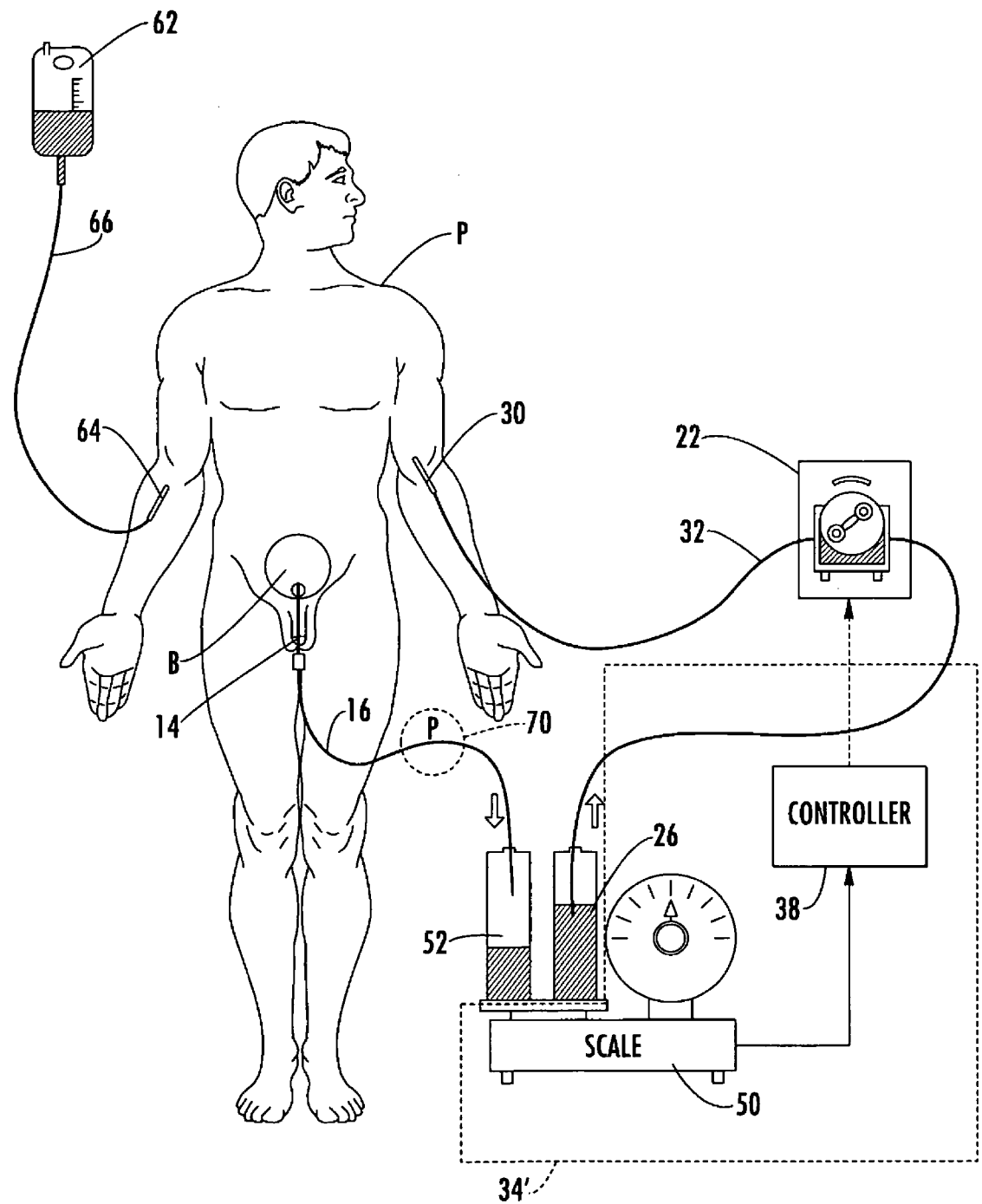
FIG. 2 is a schematic view of one embodiment of a patient hydration system in accordance with the subject invention wherein the weight of the urine output by a patient is measured and used as an input to control the infusion rate of an infusion pump.

In one example, meter 36, FIG. 1 is a weight measurement device such as scale 50, FIG. 2. Here, urine collection chamber 52 on scale 50 is connected to catheter 14 via tubing 16. Scale 50 outputs a signal corresponding to the weight of urine or the combined weight of urine and hydration fluid (in this case to maintain net-zero hydration, the scale reading should be maintained constant) or the difference between the weight of urine and the weight of hydration fluid in collection chamber 52 to controller 38. The patient hydration system of this invention may further include diuretic administration system 60 including a source 62 of a diuretic such as furosemide administered via I.V. 64 inserted in patient P and connected to source 62 via tubing 66. In alternative embodiment, tubing 66 can be connected to the patient P via hydration I.V. 30 using standard clinical techniques. Also, if desired, a urine pump such as, for example, peristaltic pump 70 can be used to urge urine from bladder B to collection chamber 52 and to automatically flush catheter 14 if it is occluded. The advantage of urine collection pump 70 is that collection chamber or bag 52 can be at any height relative to the patient P. As shown, chamber 24 containing the hydration fluid 26 can also be placed on scale 50 in an embodiment where differential weighing is used. The controller (38) electronics and software are capable of integrating urine output (for example every 15 or 30 minutes) and changing the infusion rate setting of the infusion pump 22 following an algorithm executed by the controller.

Electronic controller 22 may also incorporate a more advanced feature allowing the physician to set a desired (for example positive) hydration net goal. For example, the physician may set the controller to achieve positive net gain of 400 ml in 4 hours. Controller 38 calculates the trajectory and adjust the infusion pump flow rate setting to exceed the urine output accordingly. For example, to achieve a positive net gain of 400 ml over 4 hour, controller 38 may infuse additional 25 ml of hydration fluid every 15 minutes in addition to the volume of urine made by the patient in each 15 minute interval.

Figure 3:
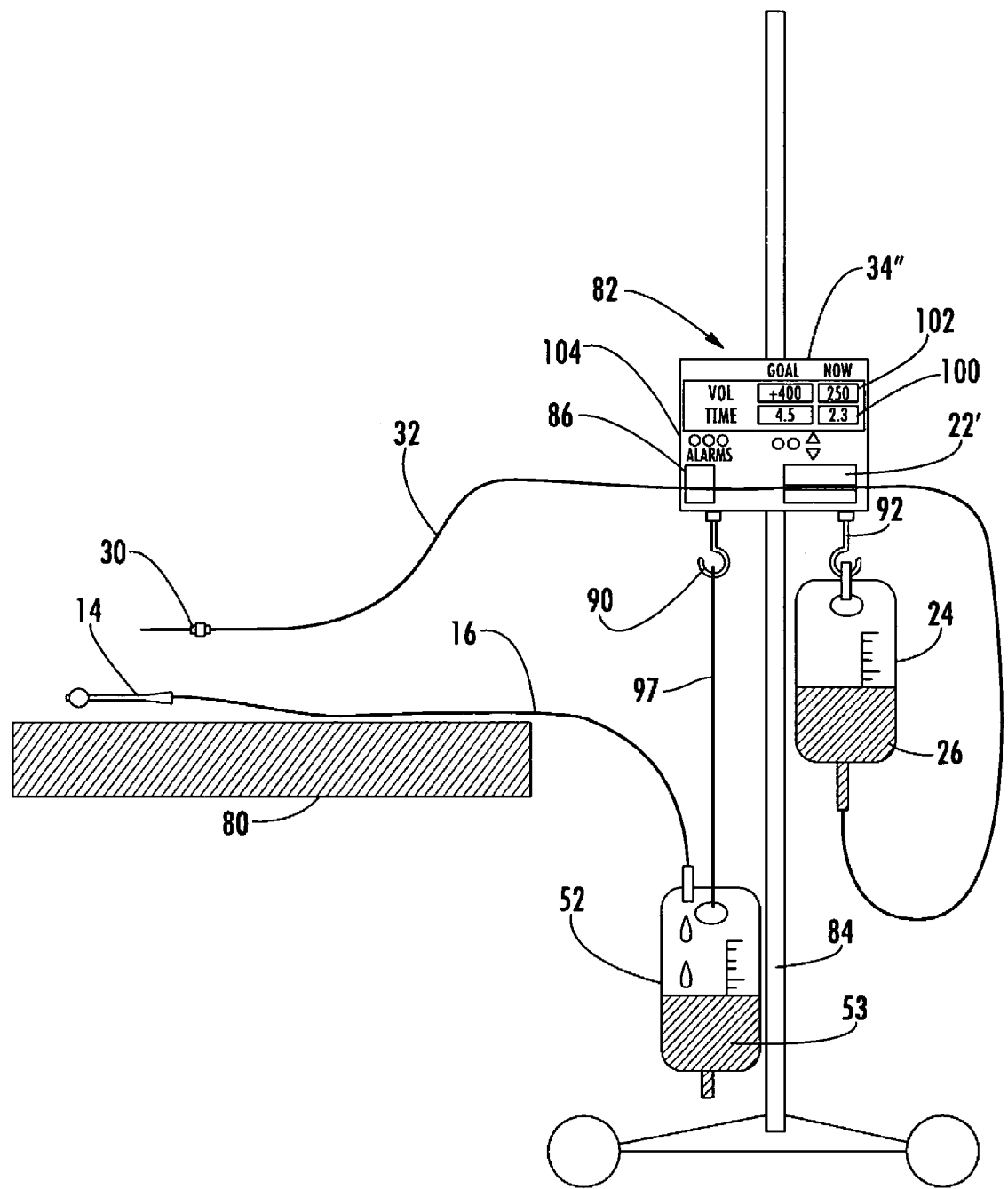
FIG. 3 is a schematic view of another embodiment of a patient hydration system in accordance with the subject invention wherein the controller and weighing mechanism are integrated in a single control subsystem unit.

In the embodiment of FIG. 3, the programmable controller and the weighing mechanisms are integrated in controller unit 34". The patient (See FIG. 1) is placed on the hospital bed or operating table 80. The hydration I.V. 30 and the urinary collection (Foley) catheter 14 are inserted using standard methods. The controller electronics and the infusion pump 22' are integrated in the single enclosure of the control subsystem 34" console 82. Console 82 is mounted on I.V. pole 84.

Control subsystem 34" may also include electronic air detector 86 that prevents infusion of air into the patient. The air detector 86 is of ultrasonic type and can detect air in amounts exceeding approximately 50 micro liters traveling inside the infusion tubing 32. In one example, air detector 86 employs technology based on the difference of the speed of sound in liquid and in gaseous media. If an air bubble is detected, the pump 22' is stopped almost instantaneously.

Console 82 may include one electronic strain gage and other weighing means to periodically detect the weight of the collected urine in chamber 52 and, another electronic strain gauge to detect the weight of the remaining hydration fluid in chamber 26. In the proposed embodiment, bag 52 with collected urine 53 and the bag 24 with hydration fluid 26 are hanging off the attachments (e.g., hooks) 90 and 92 connected to the train gauges. Cable 91 interconnects hook 90 with urine collection bag 52 to keep urine collection bag 52 below the elevation of the patient. The bags with fluids are suspended from the hooks and a system of levers translate force to weight. The strain gauges convert force into an electronic signal that can be read by controller 34". Suitable electronic devices for accurately measuring weight of a suspended bag with urine are available from Strain Measurement Devices, 130 Research Parkway, Meriden, Conn., 06450. These devices include electronics and mechanical components necessary to accurately measure and monitor weight of containers with medical fluids such as one or two-liter plastic bags of collected urine. For example, the overload proof single point load cell model S300 and the model S215 load cell from Strain Measurement Devices are particularly suited for scales, weighing bottles or bags in medical instrumentation applications. Options and various specifications and mounting configurations of these devices are available. These low profile single point sensors are intended for limited space applications requiring accurate measurement of full-scale forces of 2, 4, and 12 pounds-force. They can be used with a rigidly mounted platform or to measure tensile or compressive forces. A 10,000Ω wheatstone bridge offers low power consumption for extended battery life in portable products. Other examples of gravimetric scales used to balance medical fluids using a controller controlling the rates of fluid flow from the pumps in response to the weight information can be found in U.S. Pat. Nos. 5,910,252; 4,132,644; 4,204,957; 4,923,598; and 4,728,433 incorporated herein by this reference.

It is understood that there are many known ways in the art of engineering to measure weight and convert it into computer inputs. Regardless of the implementation, the purpose of the weight measurement is to detect the increasing weight of the collected urine 53 in the bag 52 and to adjust the rate of infusion or hydration based on the rate of urine flow.

Console 82 is also typically equipped with the user interface. The interface allows the user to set (dial in) the two main parameters of therapy: the duration of hydration and the desired net fluid balance at the end. The net fluid balance can be zero if no fluid gain or loss is desired. Display indicators on the console show the current status of therapy: the elapsed time 100 and the net fluid gain or loss 102.

The user interface may also include alarms 104. The alarms notify the user of therapy events such as an empty fluid bag or a full collection bag as detected by the weight scale. In one proposed embodiment, the urine is collected by gravity. If urine collection unexpectedly stops for any reason, the system will reduce and, if necessary, stop the IV infusion of fluid and alarm the user. Alternatively, the console can include the second (urine) pump (see pump 70, FIG. 2) similar to infusion pump 22. This configuration has an advantage of not depending on the bag height for drainage and the capability to automatically flush the catheter 14, FIG. 3 if it is occluded by temporarily reversing the pump flow direction.

Figure 4:
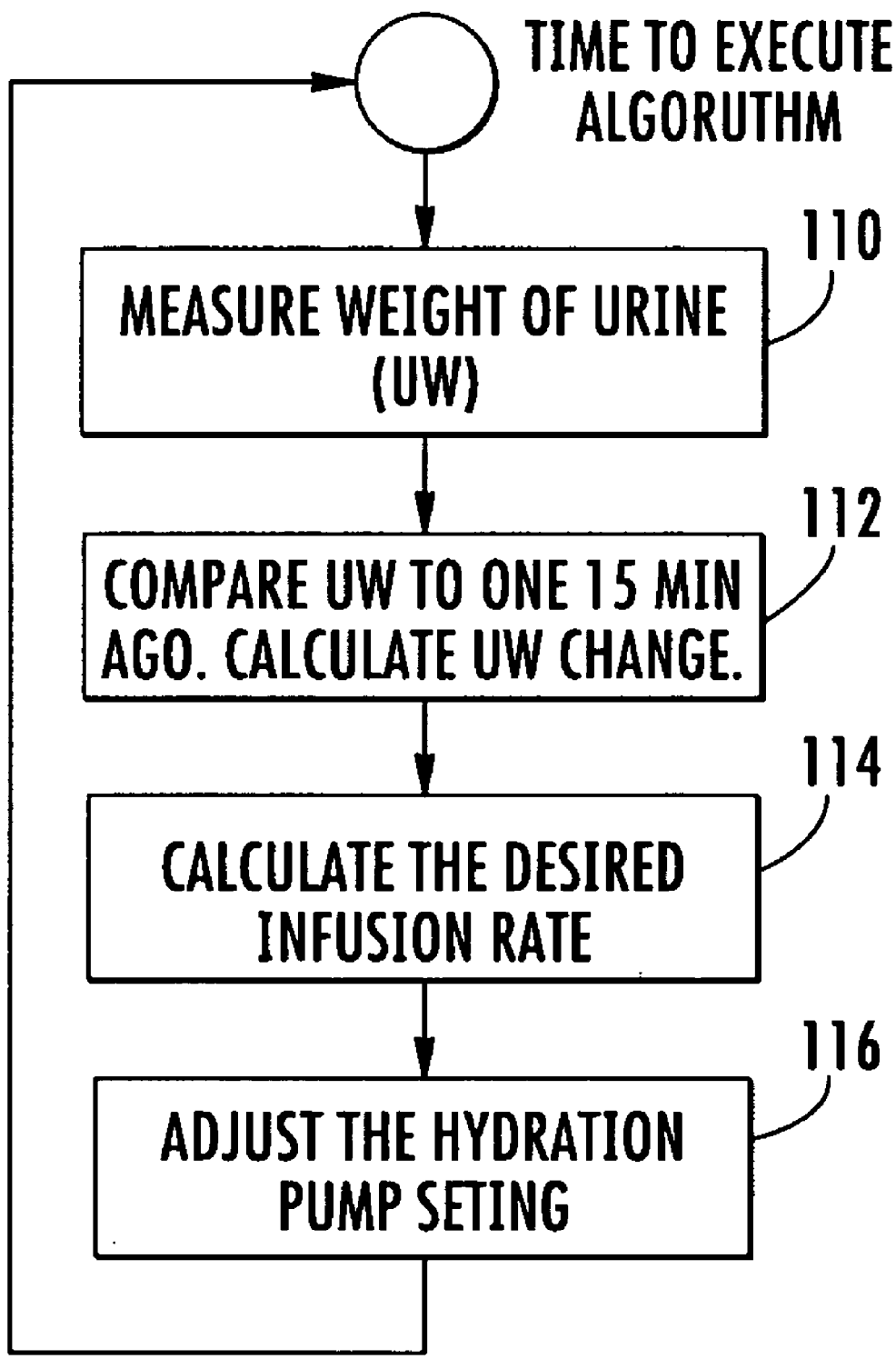
FIG. 4 is a flow chart depicting one example of the software associated with the controller of this invention and the method of adjusting the infusion rate based on the amount of urine output by the patient.

FIG. 4 illustrates an algorithm that can be used by the controller software of controller 34" to execute the desired therapy. The algorithm is executed periodically based on a controller internal timer clock. It is appreciated that the algorithm can be made more complex to improve the performance and safety of the device. Controller 34", FIG. 3 is programmed to determine the rate of change of the urine weight, steps 110 and 112, FIG. 4 to calculate a desired infusion rate based on the rate of change of the urine weight, step 114, and to adjust the infusion rate of the infusion pump 22, FIG. 3 based on the calculated desired infusion rate, step 116, FIG. 4.

Figure 5:
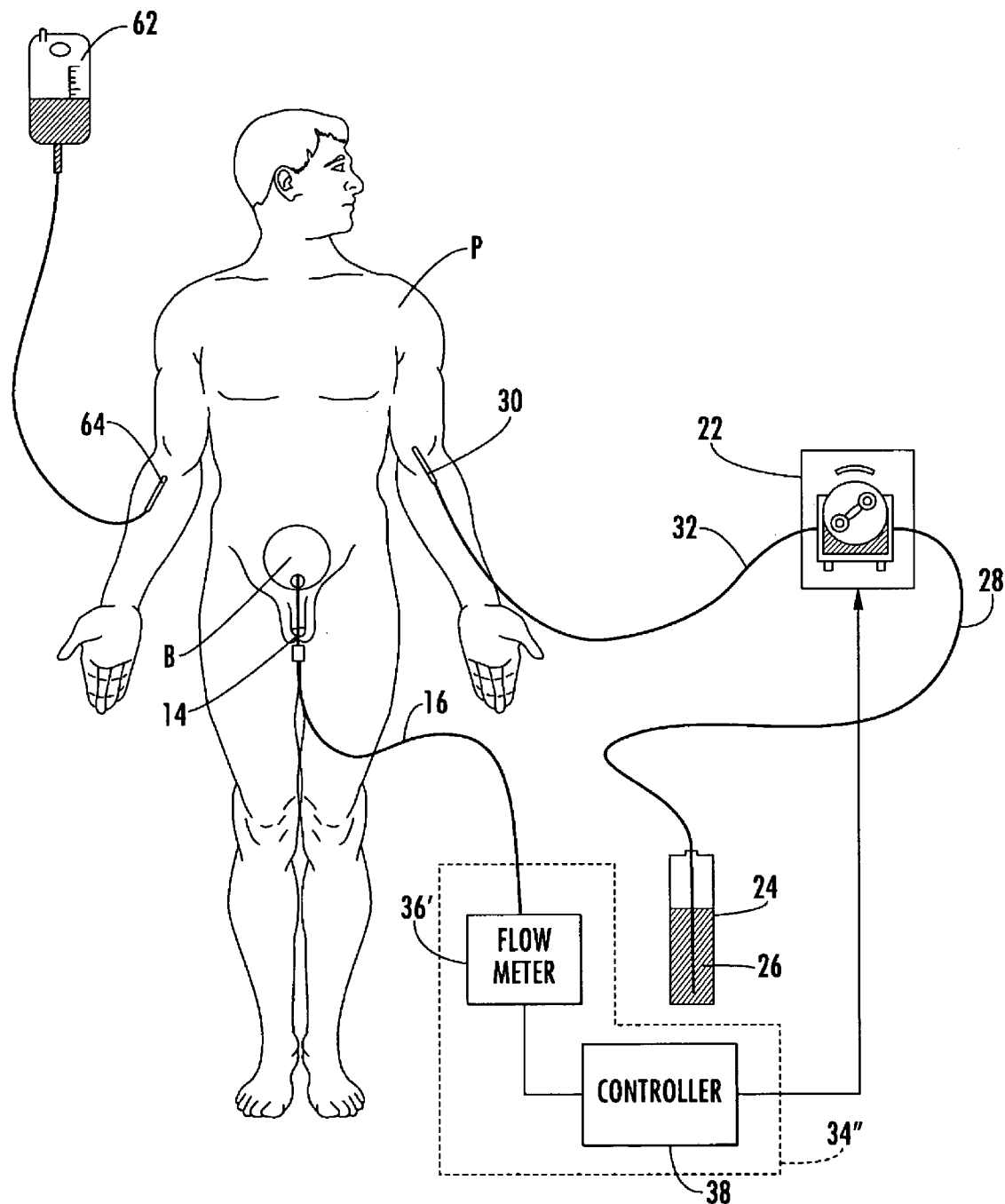
FIG. 5 is a schematic view showing another embodiment of the subject invention wherein a flow meter is used to determine the amount of urine output by the patient.

So far, the subject invention has been described in connection with the best mode now known to the applicant. The subject invention, however, is not to be limited to these disclosed embodiments. Rather, the invention covers all of various modifications and equivalent arrangements included within the spirit and scope of the appended claims. Particularly, the embodiments used to illustrate the invention use the weight of the collected urine for balancing. It is understood that it is the volume of the urine that is clinically important but the weight of the urine is equivalent for any practical purpose. For the purpose of this application, 100 grams of urine are the same as 100 ml of urine. It is believed at the time of the subject invention that measuring weight is more practical than measuring volume and that the weight is often used as a clinically acceptable substitute of volume of liquids that consist mostly of water. For practical purposes, the specific gravity (specific gravity of a substance is a comparison of its density to that of water) of urine and hydration fluids is the same as water. Those skilled in the art will realize that it is possible to measure volume directly using a meter which monitors the height of the column of the liquid in a vessel or by integrating the known volume of strokes of the pump over time. The exact meter used does not change the subject invention in regard to the balancing of urine output with hydration. Also, flow meter 36', FIG. 5 could be used to measure the urine output of patient P and a signal corresponding to the flow rate provided to controller 38. Urine flow meter 36', FIG. 5 can be one of the devices disclosed in U.S. Pat. Nos. 5,891,051; 5,176,148; 4,504,263; and 4,343,316 hereby incorporated herein by this reference.

Also a medical device manufacturer, SFM Ltd., 14 Oholiav Street, Jerusalem, 94467, Israel manufactures and markets an electronic flow meter suitable for use with this invention. According to the manufacturer SFM Ltd. the UREXACT 2000 System is an accurate electronic urine-measuring device that combines an innovative disposable collection unit with a re-usable automatic electronic meter to provide precise urine monitoring. The UREXACT 2000 is based on the ultrasonic method of measuring fluid flow.

One potential concern with the use of the embodiment shown in FIG. 3 is that the weight of hydration fluid at any give time may not always provide a reliable indication of the true amount of hydration fluid injected into the patient via pump 22'. For example, IV Pole 84 and/or hydration fluid bag 24 could be jostled affecting the strain gauge measurement, hydration fluid bag 24 could leak or, when only partially emptied, replaced with a full bag, or bag 24 may not be hanging freely from hook 92.

Similarly, the operation of pump 22' may not always provide a reliable indication of how much hydration fluid is actually injected into the patient due to inaccuracies in the pump electronics and the like.

Figure 6:
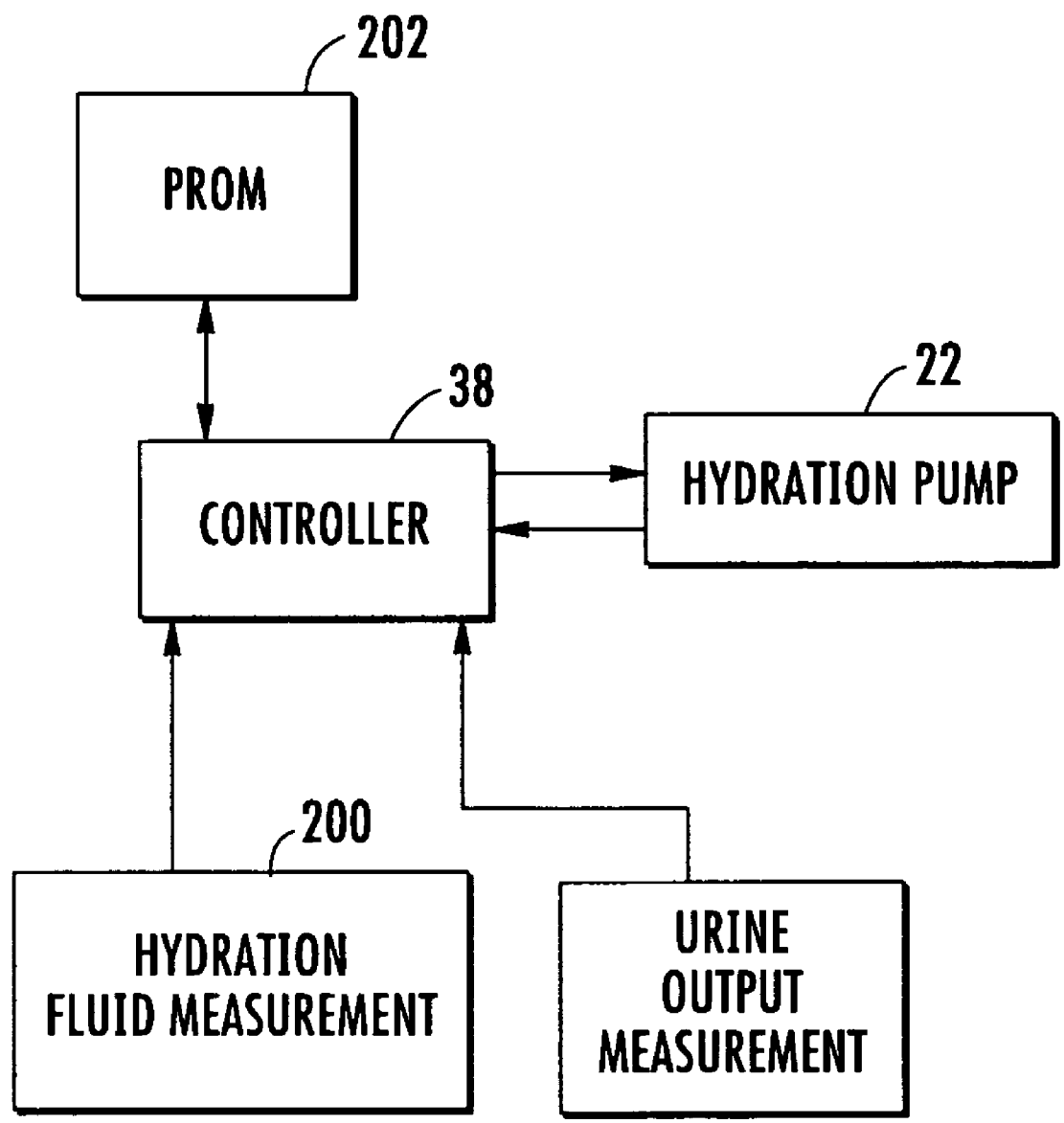
FIG. 6 is a schematic block diagram depicting one example of how the controller of the subject invention provides redundancy in the measurement of the amount of hydration fluid administered to a patient by monitoring the operation of the hydration pump and also by monitoring the weight of the source of hydration fluid.
Figure 7:
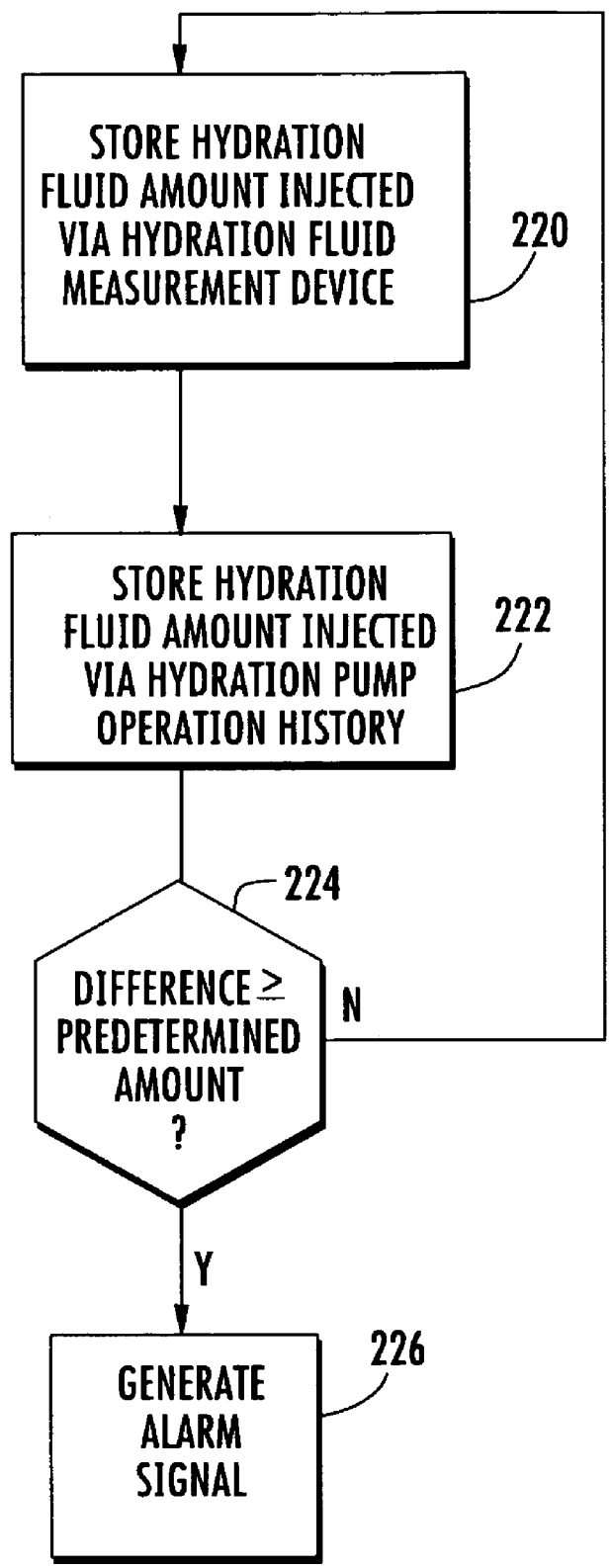
FIG. 7 is a block diagram showing the primary steps associated with the programming of the controller shown in FIG. 6.

In the subject invention, controller 38 (a microprocessor or microcontroller) in console 82, as shown in FIG. 6, controls hydration pump 22 to infuse the patient with hydration fluid based on the patient's urine output and keeps track of the hydration fluid injected in two ways to provide safety and redundancy. First, as discussed above, the weight of hydration fluid source 24, FIG. 3 is monitored as shown at 200 in FIG. 6. In addition, the operation history of infusion pump 22 is monitored by controller 38. Controller 38 may store values representing both of these measurements in a memory such as PROM 202 and controller 38 is programmed as shown in FIG. 7 to store the hydration fluid amounts administered via the hydration fluid measurement strain gauge, step 220, FIG. 7, and controller 38 is also programmed to store the hydration fluid amount administered by monitoring of the hydration pump operation history, step 222. If there is a difference between these two stored values by a predetermined amount, step 224, an alarm signal can be generated, step 226 so that the potential problem can be corrected. Controller 38 can also be programmed to output an alarm signal if, for example, the weight of saline bag indicates 50 cc of saline has been injected in the last 10 minutes but the pump operation history indicates only 20 cc of saline has been injected in the last 10 minutes. This condition would likely indicate the saline bag is not hanging free on hook 90, FIG. 3. The alarm signal can trigger a nurse to check the condition of the saline bag.

In another possible scenario, the pump operation history does not equate to an amount of hydration fluid administered commensurate with the weight of the saline bag. In such a scenario, controller 38 can be programmed to reset the pump and then adjust the operation of the pump to inject hydration fluid based on the patient's urine output and the weight of the saline bag.

Typically, the controller is also configured to operate pump 22 at predetermined maximum and minimum infusion rates irrespective of the weight of the saline bag (determined via a first strain gauge), the weight of the urine bag (determined by a second strain gauge), or the pump operation history. An acceptable maximum infusion rate may be 60 liters per minute in any 15 minute time period or 22 liters per hour at any time. An acceptable minimum infusion rate may be 1 milliliter per hour per kilogram of patient weight to keep the patient's vein open at the site of the infusion IV needle 30, FIG. 3 irrespective of the weight of the urine bag.

Figure 8A:
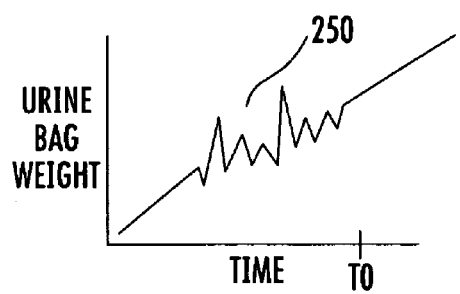
FIGS. 8A-8D are graphs showing signals indicative of an abnormal urine output weight measurement.

It is preferable that in any embodiment the hydration system be portable since patients are often moved in and out and about the cath lab. When the embodiment of FIG. 3 is employed, for example, there are conditions and events wherein the weight of urine bag 52 may not be indicative of the true amount of urine output by the patient at any given time. FIG. 8A shows a signal received by the controller from a strain gauge which measures the weight of urine bag 52, FIG. 3 in a situation where the urine bag has been jostled. The signal portion 250, FIG. 8A is indicative of an abnormal patient urine output measurement.

Figure 8B:
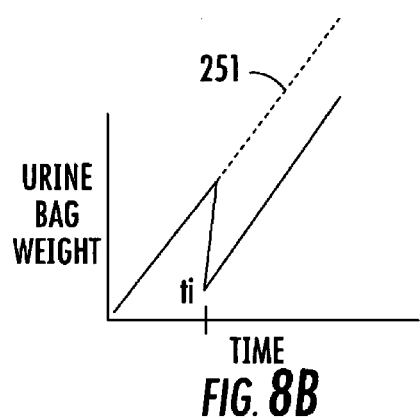
Figure 8C:
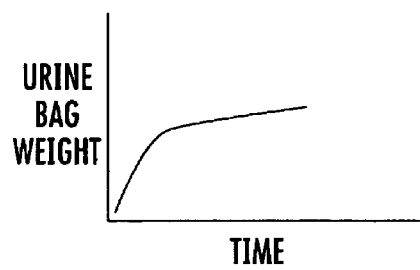
Figure 8D:
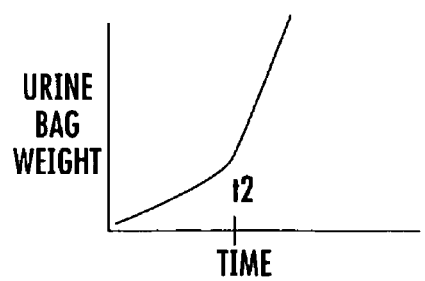

FIG. 8B shows another abnormal patient urine output measurement signal indicative of a urine bag 52, FIG. 3 which has been emptied at time $t_1$. FIG. 8C shows another abnormal patient urine output measurement signal indicative of a potential problem since the patient's urine output is not increasing over time as expected. FIG. 8D shows another abnormal patient urine output measurement indicative of a potential problem since the patient's urine output is increasing, beginning at time $t_2$, at a rate higher than expected.

Similarly, it is possible that the weight of hydration fluid bag 24, FIG. 3 may not always be indicative of the true amount of hydration fluid administered to the patient in any given time period.

Figure 9A:
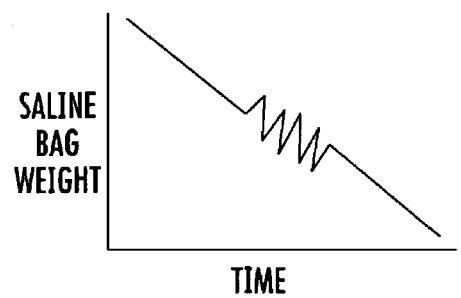
FIGS. 9A-9B are graphs showing signals indicative of an abnormal hydration fluid bag weight measurement.

FIG. 9A is representative of the signal received by the controller from a strain gauge which measures the weight of hydration fluid bag 24, FIG. 3 in the case where the hydration fluid bag has been jostled.

Figure 9B:
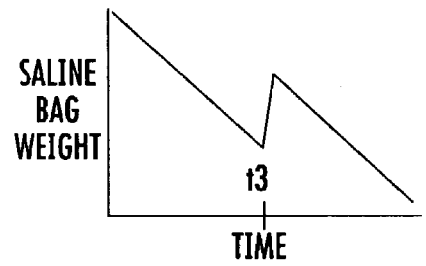

Another abnormal hydration fluid measurement is shown in FIG. 9B which indicates that at time $t_3$ an empty hydration fluid bag has been replaced with a full hydration fluid bag.

In accordance with the preferred embodiment of the subject invention, controller 38, FIG. 6 is responsive, via the strain gauges or other measurement devices, to the urine bag weight and also the weight of the hydration fluid bag to achieve a predetermined hydration balance as discussed above, step 260, FIG. 10. Controller 38, FIG. 6 is also programmed to detect a) abnormal patient urine output measurements like those of FIGS. 8A-8D, step 222, FIG. 10 and b) abnormal hydration fluid measurements like those of FIGS. 9A-9B, step 264, FIG. 10. The controller is further programmed to take corrective action, steps 266 and 268 in response to these abnormal measurements. The corrective action typically depends on the specific abnormal indication. In the case of FIG. 8A, which likely is indicative of a jostled urine collection bag, the urine output measurement is sharply varying and the controller can be programmed to control the infusion pump to hydrate the patient at a preset minimum infusion rate, for example, 1 milliliter per hour per kilogram of patient body weight. This safe minimum level is often referred to as KVO for "keep vein open" in clinical practice. After the signal settles down as shown at time $t_0$ in FIG. 8A, the controller is programmed to hydrate the patient at an increased rate thereafter to achieve the predetermined hydration balance. The controller software calculates the amount of urine made by the patient during the occurrence of the sharply varying urine output signal and increases the infusion rate by controlling the infusion pump to give back to the patient the volume lost by the patient, the "owed volume". The automatic administration of the "owed volume" exemplifies the corrective action. After the predetermined hydration balance is restored, the infusion rate is returned to the normal level so that the hydration fluid input level matches the urine output level plus or minus any desired net gain or loss. Urine output fluctuates in time and balancing is, in reality, dynamic based on small time increments. They can be less than 1 second long. At the end of each control interval, a new correction can be introduced by controller 38 to the infusion pump speed to achieve the goal of balancing in a smooth reasonable way at an allowed rate of change. It is not practical to administer all the "owed" volume immediately. The controller software gives back fluid in small safe increments over time, for example, a safe limit of no more than 250 milliliters over 15 minutes or a flow rate of no more than 6 liters per hour. Methods of such dynamic control are implemented in the controller software and the safe limits of infusion imbedded in the software or set by the user via the user interface of console 82, FIG. 3.

In another example, when controller 38, FIG. 6 detects the abnormal signal of FIG. 8A, the controller can be programmed to ignore errant signal portion 250 and control infusion pump 22, FIG. 6 to maintain infusion at the rate prior to errant signal portion 250, FIG. 8A. After the errant signal is no longer detected, infusion continues in accordance with FIG. 4. Rejection of the errant signal is another example of the corrective action by the system.

FIG. 8B illustrates a signal received by the controller indicative of a urine bag that has been at least partially emptied. Other possibilities include a urine collection bag which leaks or a drain valve that has not been completely closed. In such as situation, the controller software can be configured to control the operation of the infusion device based on the patient's urine output before and after the urine bag was emptied to achieve the predetermined hydration balance. That is, the controller software extrapolates the urine bag weight as shown at 251 in FIG. 8B to provide a proper indication of the patient's urine output.

In FIG. 8C, the urine bag weight is not increasing as expected and the controller software recognizes and detects this abnormal patient urine output measurement and generates an alarm signal to be displayed on console 82, at display area 86, FIG. 3. Similarly, in FIG. 8D the urine bag weight sharply increases at time $t_2$ and the controller software is configured to generate another alarm signal.

In the case of abnormal hydration fluid measurement, FIG. 9A is indicative of a source of hydration fluid which has been jostled and the controller software is configured to take corrective action in a form of an alarm signal, for example.

Figure 11:
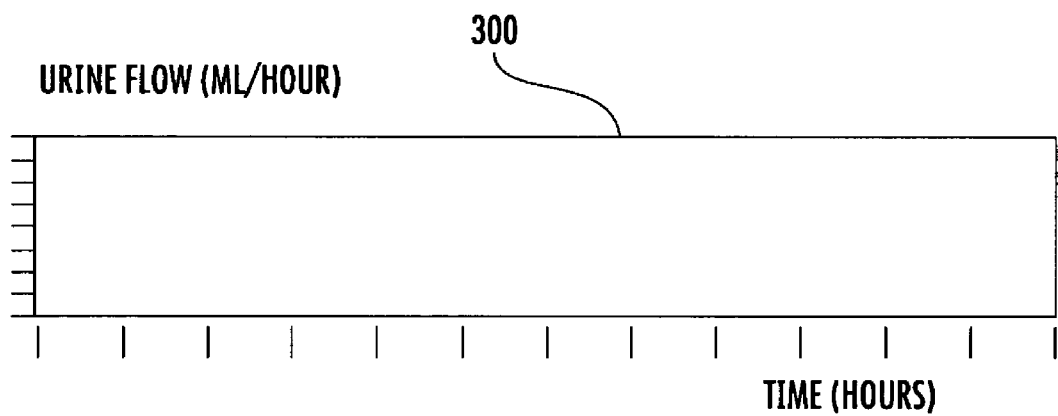
FIGS. 11-12 are simplified graphs depicting how the hydration fluid administration rate is increased after a disruption in accordance with the subject invention.
Figure 12:
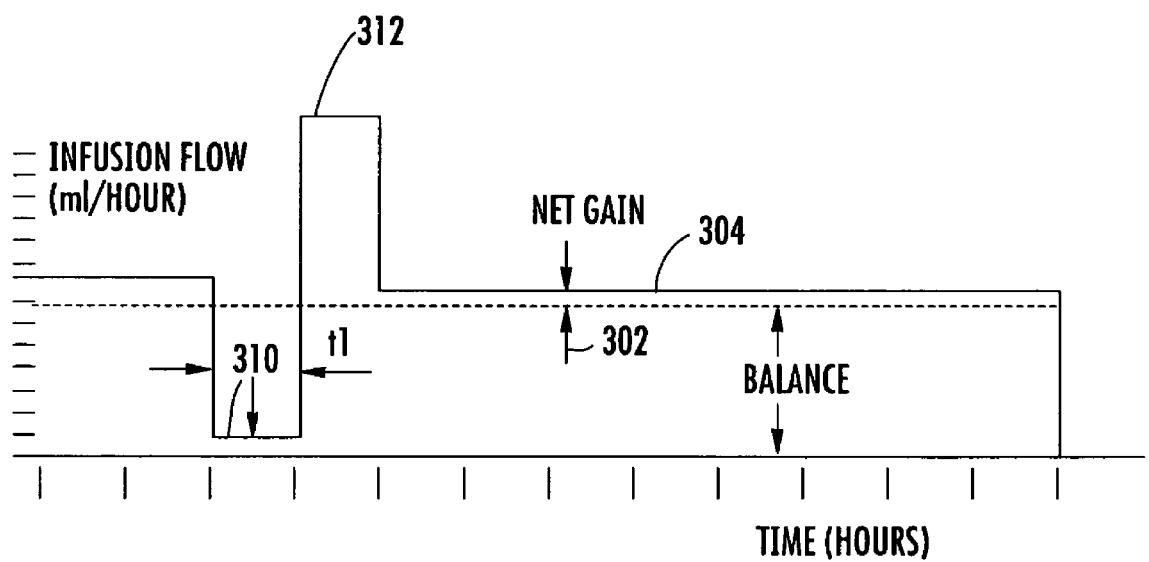

FIGS. 11-12 illustrate the concept of "catching up" or "giving back" the hydration fluid "owed to the patient" when balancing is for some reason temporarily disrupted. Ideally, as the patient makes urine continuously at level 300 hydration would be balanced continuously. In reality, the process is frequently interrupted when the urine bag is full and drained, bags with hydration fluid are empty and replaced or when the patient is transported and accurate measurements of weight become impossible. In the cathlab environment patients are frequently moved from one location to another. It is an object of this invention to enable balanced hydration of the patient throughout the normal flow of the cathlab procedure.

As described above, balancing is implemented via periodic reading of weight scales. In the proposed example, bag 52, FIG. 3 with collected urine 53 and the bag 24 with hydration fluid 26 are hanging off the hooks 90 and 92 connected to the weight scales. The bags with fluids are suspended from the hooks that translate force to scales such as load cells with strain gages. Strain gage converts force into an electronic signal that can be read by the controller. Suitable electronic devices for accurately measuring weight of a suspended bag with urine are available from Strain Measurement Devices Inc., (Meriden, Conn.). In the preferred embodiment two strain gages model SMD S300 designated by this manufacturer as Load Cells with Integral Overload Protection and 2 Kg capacity are used to measure and balance weight (and volume) of fluid. These devices include electronics and mechanical components necessary to accurately measure and monitor weight of containers with medical fluids such as one or two-liter plastic bags of collected urine and hydration fluid. When the patient and the device are moved weight scales are effected by motion artifacts (inertia) and electronic signals often become unreliable.

The patient's hydration rate, FIG. 12 is set to the sum of balancing volume equal to urine output 300, FIG. 11 and net gain 304 during normal operation. During the time period $t_1$, a disruption is detected. For example, the urine bag may be drained or the weight scale readings are unreliable because of motion.

In one embodiment, the controller software responds in the following way.

The disruption is detected and the infusion rate is set to safe minimum level 310 often referred to as KVO for "keep vein open" in clinical practice. For example, KVO can be set to 1 ml/hour per kg of body weight or just 70 ml/h. When the end of the disruption is detected, the software calculates the amount of urine made by the patient during the disruption time using weight measurement. The system increases the infusion rate as shown at 312 to give back the volume lost by the patient—"owed volume". After the balance is restored, the infusion rate is returned to normal level such as the balance plus the desired net gain 304.

Figure 10:
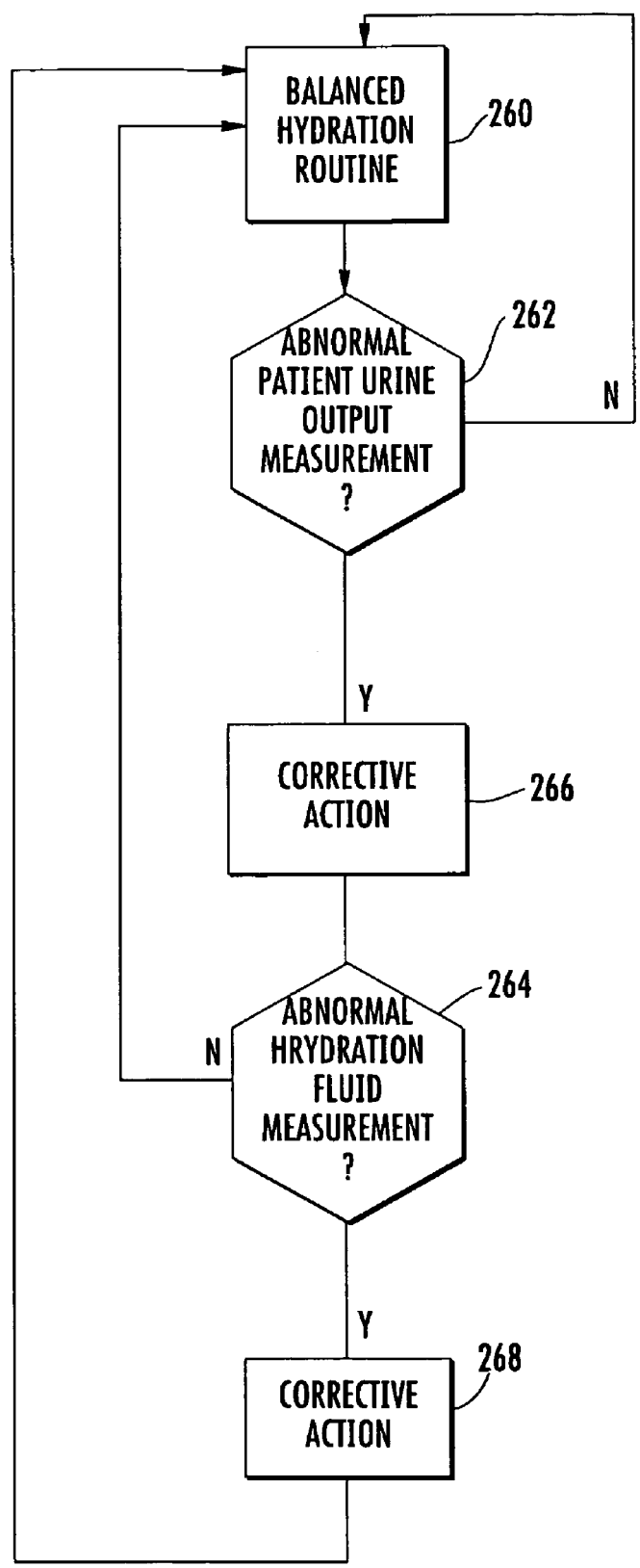
FIG. 10 is a flow chart showing the primary steps associated with the programming of the controller shown in FIG. 6.

The process so illustrated by FIG. 10 is greatly simplified to emphasize the point of restoring balance after disruption. It is understood that urine output fluctuates in time and balancing is in reality dynamic based on small time increments that can be less than one second long. At the end of each control interval new correction is introduced to the infusion pump speed to achieve the goal of balancing in a smooth reasonable way at an allowed rate of change. Even if the pump capacity allows it, it is not practical to infuse all the "owed" volume immediately. The software controls the infusion device to give back fluid in small safe increments spaced over time. For example safe limit can be set to no more of 250 ml over 15 minutes or flow rate of no more than 6 liters per hour. Methods of such dynamic control of volume are known in the field of control engineering and embedded real time software. Safe limits of therapy can be embedded in the software by the manufacturer or set by the user via user interface.

If the disruption is caused by the user changing an infusion fluid bag, infusion flow during the disruption is set to zero. The user can force this condition by using the ON/OFF button on the console. The pump should be stopped while user is spiking a new bag, otherwise air will be pumped. If a disruption is caused by user draining the urine bag, the infusion flow can be set to KVO level. The user can force this condition by pushing the PAUSE button on the console. Alternatively this condition can be automatically detected by the weight scale sensing abrupt reduction of urine bag weight. If the urine bag is full (as detected by maximum weight), the system automatically stops balancing and switches to the KVO mode. An alarm is issued to remind user to drain the bag some time before the bag is full. For example, if the bag volume is 2 liters, alarm can be issued when the urine weight corresponds to 1.8 liters of urine.

During pause mode, the controller software generates a low volume beeping alarm. After 15 minutes, the software increases the volume to high to attract attention of the user. At the same time visual indication such as a "PAUSE" message or a Pause LED is used to inform the user of the reason for device beeping.

Upon exit from Pause mode and into run mode, the software can automatically adapt to the infusion and urine bag weight changes to correctly resume hydration control. There are several ways to detect disruption caused by motion. In a simpler embodiment system software detects that the system console is unplugged from the AC wall outlet and operating on batteries. During battery operation balancing is turned off and KVO rate of infusion is set. When AC cord is plugged back in the disruption is considered to be over and the collected urine is measured and balanced as quickly as practical and safe. Alternatively the device can be equipped with a transport key commend activated by user. In a somewhat more complex embodiment software can analyze and detect fluctuations of weight caused by motion inertia and suspend balancing until reliable measurements are re-established.

A User Interface

Figure 13:
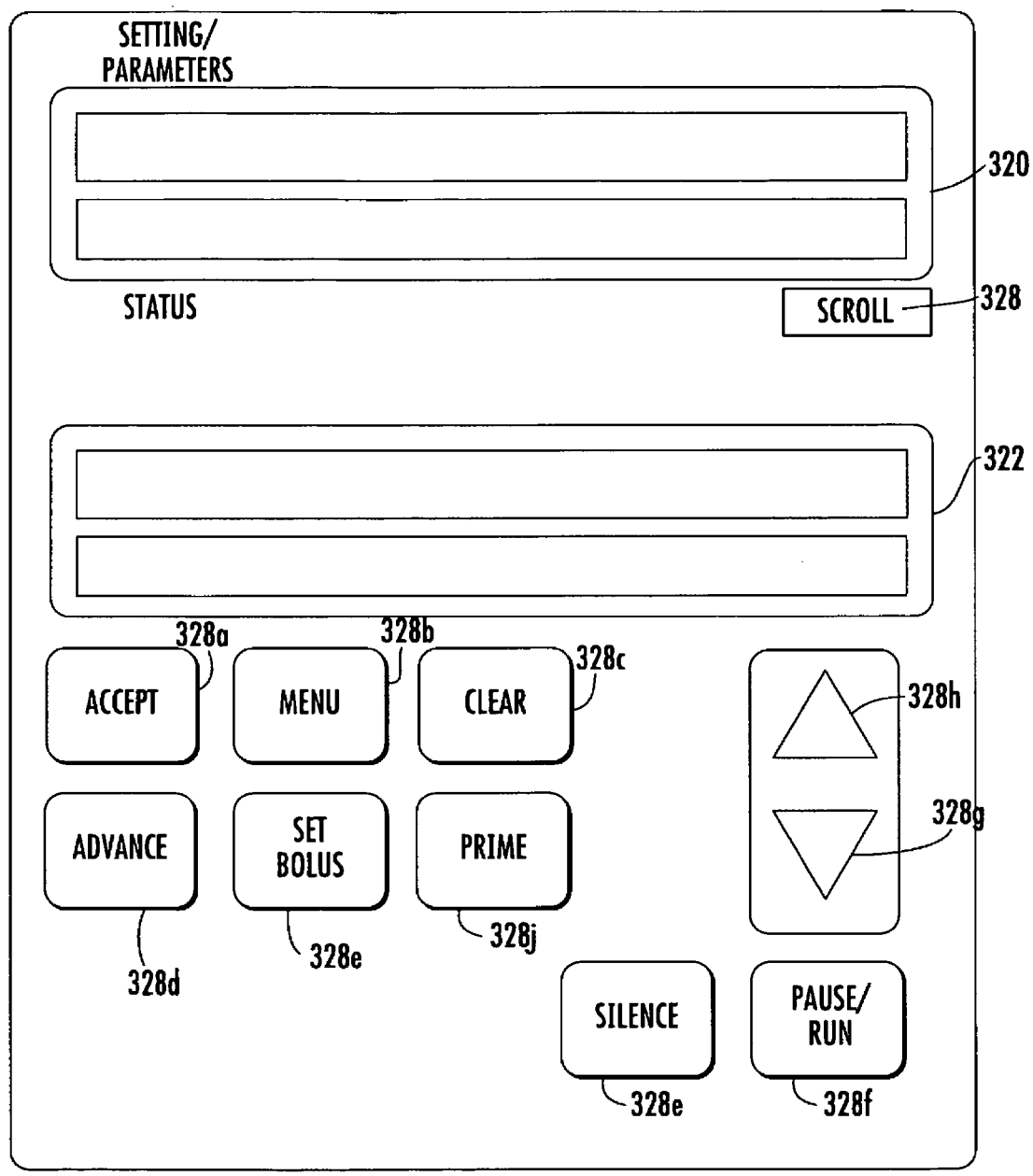
FIG. 13 is a schematic front view of an example of a user interface in accordance with the subject invention.

FIG. 13 illustrates an example of a user interface of the proposed embodiment. In the proposed embodiment, the user interface consists of two Liquid Crystal Displays 320 and 322 and 11 function keys or buttons 328a-328j. The LCDs can be 2×24 LCD with LED backlight and 3.2×5.55 mm characters part number NHD-0224B0-FSW-GBW from New Haven Display International (Hoffman Estates, Ill.).

The function keys have following functions. Scroll Key 328i is intended to be used to scroll through the system parameters displayed on 320. Parameters such as total urine made, time of therapy, net balance can be displayed at any time by user command.

Menu Key 328b is intended to be used to view the system setting's menu. When in the menu mode user can change parameters of therapy such as desired hourly net gain, bolus amount or maximum amount of hydration allowed. Accept Key 328a is intended to be used to enter (accept) inputs. Clear Key 328c is intended to be used to cancel inputs and clear alarms. Up Arrow Key 328h is intended to be used to increment settings and navigate the menus and Down Arrow Key 328g is intended to be used to decrement settings and navigate the menus. Advance key 328d is intended to allow manual operation. While key is pressed system rotates the pump at a preset speed. This mode is used to manually prime the circuit with fluid or advance air bubbles through the tubing.

For example, while the advance key is pressed, the software may run the pump at 60 ml/min. Advance mode may be stopped by releasing the advance key or when a timeout of 30 seconds of continuous operation has elapsed. After a time out, advance mode may be allowed after the advance key is released for 2 seconds.

Set Bolus Key 328e is intended to allow setting of the bolus amount and duration. Pause Key 328f is intended to pause the running system or resume operation if paused. After key 328f is pressed, the system switches to fixed KVO infusion rate, no balancing is performed. This key can be used to suspend balancing while urine bag is drained. It can also be used when patient is moved and signals from weight scales are disturbed. When the system is paused it emits a beeping sound to alert the user. The status LCD displays a message indicating the pause state and the elapsed time in the pause state. Run/Stop Key 328f is intended to run the system if stopped and stop the system if running.

Prime Key 328j is intended to initiate a priming process and Silence Key 328e is intended to silence the alarm audio. The prime Key initiates priming of the circuit with fluid to purge air. The software may enter prime mode to execute the prime test before entering run mode, if a new patient is selected or if the user has pressed the prime key. The prime mode may be cancelled by pressing the stop key.

In order to perform the prime test, the user connects the infusion output (tubing 32 on FIG. 3) to the urine input (tubing 16 on FIG. 3). Fluid path is set to pump from hydration bag 26 into urine bag 53. The software may operate the pump at a speed of 60 ml/min for a period of at least 2 minutes. This time is sufficient to fill the IV set with fluid and check the weight scale inputs. (The measured hydration fluid volume is expected to reduce while the measured urine output volume is expected to increase by the corresponding amount. Thus the pump and weight scales are tested). If the difference between the change in expected weights and actual weights is more than, for example, 20%, the software may generate an alarm. After priming, the controller software may display a message to the user that priming is completed and the system is ready for use. The prime test may complete execution within 5 minutes. The controller software may perform an air detector (86 on FIG. 3, which is in the fluid path) test and generate an alarm if it fails. The air detector is tested using the test signal which forces a liquid to air transition. The software may also test the operation of the pressure sensor during priming and generate an alarm on failure.

An Exemplary Circuit Architecture

Figure 14:
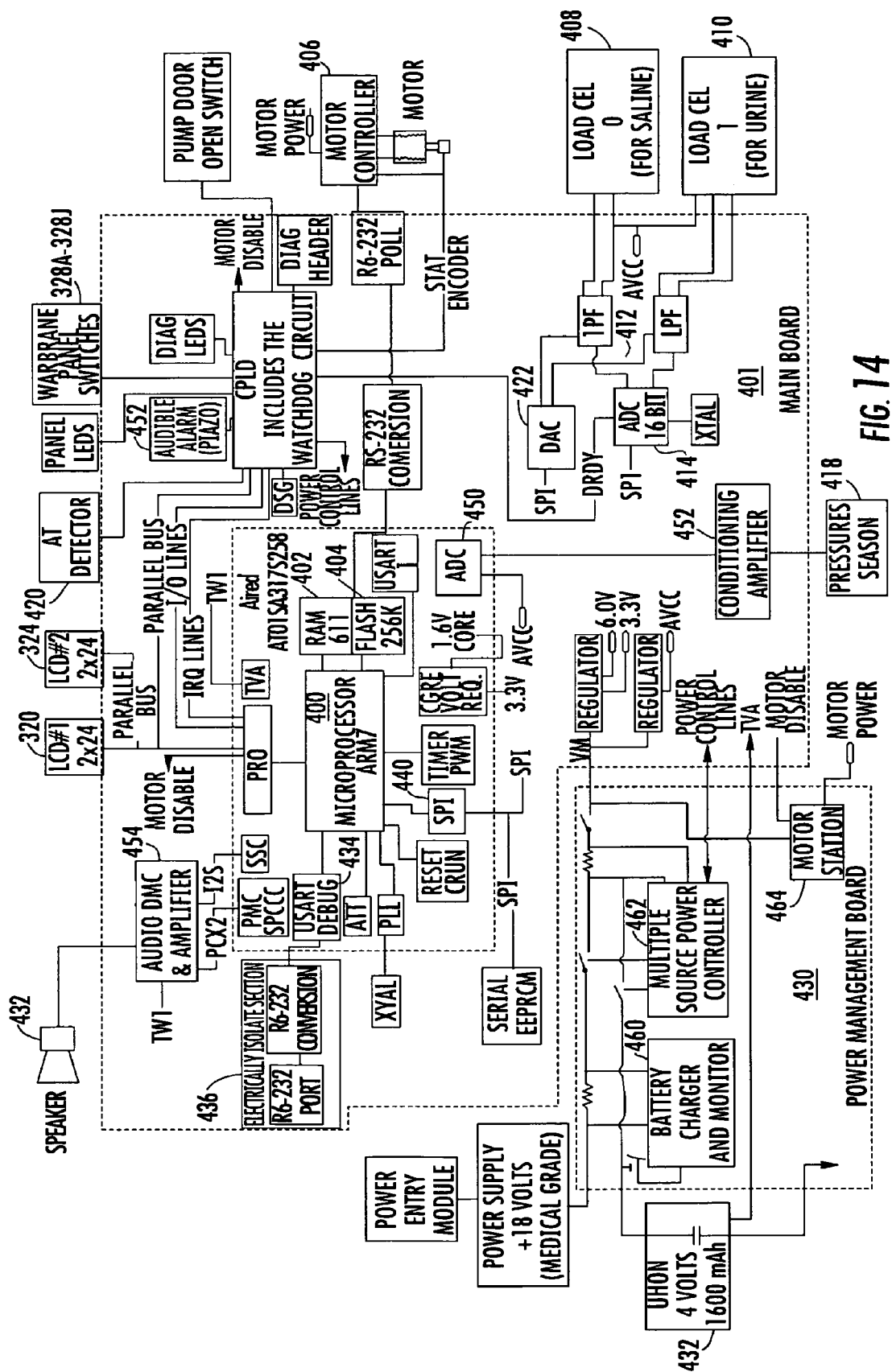
FIG. 14 is a block diagram of an example of a main printed circuit board for an embodiment of a hydration system in accordance with this invention.

In one particular example, the main circuit board for controller unit 82, FIG. 3 is shown in FIG. 14. Microprocessor 400 is an Atmel AT91SAM7S256 with an ARM7 core, 64 Kbytes internal RAM 402 and 256 Kbytes internal Flash 404. Infusion pump motor controller 406 is an off the shelf brushless DC motor controller which gets power from power management board 430 and uses internal RS232 interface to communicate with main microprocessor 400.

The load cell outputs for urine bag 52, FIG. 3 and saline bag 24 (load cells 408 and 410, FIG. 14) are amplified in differential circuit 412 and a signal is applied to differential analog to digital converter 414. Programmable logic device (CPLD) 416 is a Xilinx XC95144XL-10 TQ100. Pressure sensor 418 is a medical grade silicon pressure sensor. The sensor is supplied with 0.910 mA current from a high impedance current source to produce 2.3 V at 20 psi on the output of the instrumentation amplifier. Due to the circuit topology there is a constant offset of about 0.910V at the IA output at zero pressure. This offset is eliminated in the software. Air bubble detector 420 with its amplifier board is an off the shelf unit.

Each load cell 408, 410 can be compensated up to +/−1.49 kg by using DAC MAX525 422. This compensation is used to cancel out an offset caused by the load cell offset and gain errors.

At first power up, DAC MAX525 422 is set to middle scale for all the outputs. This step assures no effect on the offset in the load cell circuit. Saline and urine channels are compensated by pairs of DACs arranged in push-pull circuit giving the ability of positive and negative offset compensation. The preferred compensation can be achieved by iterative method. Using linear equation method may be sufficient to keep ADC 414 full scale in linear range.

Power Management board 430 contains all the circuit controlling operations of charging Lithium-Polymer battery 432 and switching between AC and battery power. The main power supply is a medical grade high-efficiency switching power supply. The Displays 401 and 403 and 8-Ohm speaker 432 are controlled by the main microprocessor 400. Piezo buzzer 452 is implemented to signal fault conditions which require operator attendance. Microprocessor 400 has a UART serial port connector 434 and an RS232 transceiver buffer 436 connects this port to a PC.

Microprocessor 400 interfaces with the external pins via its 32 PIO pins. These pins may have different functions as configured by software. Table 1 shows the functions wired to the PIO pins in the hardware. The shaded boxes in the table show the selections for each pin as "Peripheral A," "Peripheral B" or assigned as an "I/O" pin. Note that the direction of the I/O pins may be input, output or bi-directional depending on pin function.

TABLE 1

Microprocessor PIO Pin Assignments

| I/O Line | Net | Function | Periph A | Periph B | Other | I/O Pin | Pin # |
|---|---|---|---|---|---|---|---|
| PA0 | PB_EN_LCD1 | Parallel Bus Enable for LCD #1 | PWM0 | TIOA0 | Hi D | I/O | 48 |
| PA1 | MLED1 | LED1 => Warning; Red LED on front panel | PWM1 | TIOB0 | Hi D | I/O | 47 |
| PA2 | MLED2 | LED2 => Power; Green LED on front panel | PWM2 | SCK0 | Hi D | I/O | 44 |
| PA3 | TWD | Two Wire Data | TWD | NPCS3 | Hi D | | 43 |
| PA4 | TWCK | Two Wire Clock | TWCK | TCLK0 | | | 36 |
| PA5 | RXD0 | RS-232 RX 0 (motor control) | RXD0 | NPCS3 | | | 35 |
| PA6 | TXD0 | RS-232 TX 0 (motor control) | TXD0 | PCK0 | | | 34 |
| PA7 | mp_io1 | Reset to CPLD and ADC | RTS0 | PWM3 | | I/O | 32 |
| PA8 | PB_EN_LCD2 | Parallel Bus Enable for LCD #2 | CTS0 | ADTRG | | I/O | 31 |
| PA9 | RXD1 | RS-232 RX for PC I/F | RXD1 | NPCS1 | | I/O | 30 |
| PA10 | TXD1 | RS-232 TX for PC I/F | TXD1 | NPCS2 | | I/O | 29 |
| PA11 | ADC_CS# | SPI chip select to ADC | NPCS0 | PWM0 | | | 28 |
| PA12 | MISO | SPI data to uP | MISO | PWM1 | | | 27 |
| PA13 | MOSI | SPI data from uP | MOSI | PWM2 | | | 22 |
| PA14 | SPCK | SPI clock | SPCK | PWM3 | | | 21 |
| PA15 | I2S_WS | Audio I/F word select | TF | TIOA1 | | I/O | 20 |
| PA16 | I2S_SCK | Audio I/F serial clock | TK | TIOB1 | | I/O | 19 |
| PA17 | I2S_SD | Audio I/F serial data | TD | PCK2 | AD0 | | 9 |
| PA18 | CLK_AUD_DAC | Clock for the Audio DAC | RD | PCK2 | AD1 | I/O | 10 |
| PA19 | FIQ | Power Failure interrupt => Power loss in 50 ms. | RK | FIQ | AD2 | I/O | 13 |
| PA20 | IRQ0_IO | Air detector sense line | RF | IRQ0 | AD3 | I/O | 16 |
| PA21 | MTRSHTDWN# | Motor Shutdown (Low = shutdown) | RXD1 | PCK1 | | I/O | 11 |
| PA22 | PROM_CS# | SPI chip select to EEPROM | TXD1 | NPCS3 | | | 14 |
| PA23 | PB_D0 | Parallel Bus Data bit 0 | SCK1 | PWM0 | | I/O | 15 |
| PA24 | PB_D1 | Parallel Bus Data bit 1 | RTS1 | PWM1 | | I/O | 23 |
| PA25 | PB_D2 | Parallel Bus Data bit 2 | CTS1 | PWM2 | | I/O | 25 |
| PA26 | PB_D3 | Parallel Bus Data bit 3 | DCD1 | TIOA2 | | I/O | 26 |
| PA27 | PB_EN_CPLD | Parallel Bus Enable for CPLD | DTR1 | TIOB2 | | I/O | 37 |
| PA28 | PB_RW | Parallel Bus Read/Not Write | DSR1 | TCLK1 | | I/O | 38 |
| PA29 | PB_RS_AS | Parallel Bus RS or AS | RI1 | TCLK2 | | I/O | 41 |
| PA30 | ADC_DRDY#(IRQ1) | ADC Data Ready (active low) | IRQ1 | NPCS2 | | I/O | 42 |
| PA31 | DAC_CS# | SPI chip select to DAC (Note: MP_IO2 line to CPLD) | NPCS1 | PCK2 | | I/O | 52 |

ADC 44 is used to read the two load cells 408 and 410. Table 2 lists the purpose of the external ADC device inputs.

TABLE 2

External ADC Input Assignments

| Channel Number | Input | Purpose |
|---|---|---|
| 0 | Load Cell 0 | Saline Bag Weight |
| 1 | Load Cell 1 | Urine Bag Weight |

ADC 414 is accessed from microprocessor 400 via the SPI port 440 using the chip select signal "ADC_CS#." This chip select and the SPI interface are connected via the microprocessor's PIO interface (see Table 1).

The ADC ready is connected to the microprocessor physically through CPLD 416 but is unchanged by the CPLD and is provided to the microprocessor IRQ1 line as shown in the PIO pin list, Table 1.

Table 3 lists the register settings required for ADC operation.

TABLE 3

External ADC Device Register Settings

| | Function | Configuration Register (Hex) | Filter Register (Hex) |
|---|---|---|---|
| Standard 2-Channel Operation | Channel 1 | C6 | 33 |
| | Channel 2 | 56 | 33 |
| Operational Test | Channel 1 | 4000C6 | 33 |
| | Channel 2 | 800056 | 33 |

ADC 450 inside microprocessor 400 is used to input data from pressure sensor 418, which is wired to the microprocessor's ADC4 input through conditioning amplifier 452. This input line is direct to the internal ADC and does not go through the PIO interface. Also, to verify the analog voltage (AVCC) in working is checked by measuring half the value on the ADC input. An SPI quad 12-bit DAC 422 is used set offset compensation on each channel.

Sound is generated by the Main board 401 in two ways. One way is strictly for an alarm function from CPLD watchdog circuitry 416 and controls piezo sound device 452. The second way is more versatile and is controlled by microprocessor 400 and uses audio DAC 454 device to speaker 432. This speaker output maybe used for general purpose sounds as well as a full feature alarm and alert sounds.

The I2S audio data output port from the microprocessor is connected to audio DAC 454 to control and generate the sound. Additionally, DAC volume is controlled via a Two-Wire Interface (TWI) also from the microprocessor to the audio DAC. Audio DAC 454 may be a Maxim MAX9850 with its output to a Texas Instruments TPA6211A1 mono audio amplifier to drive a speaker.

The audio DAC requires a clock in the range between 8.448 and 40 MHz and this clock is connected to the DAC from the microprocessor on the PCK2 line from the Programmable Clock Output Controller of the PMC module. A sampling frequency of 8 kHz should be used for the audio DAC to minimize the size of the data required.

Microprocessor settings for Audio DAC 454 are list in Table 4.

Figure 15:
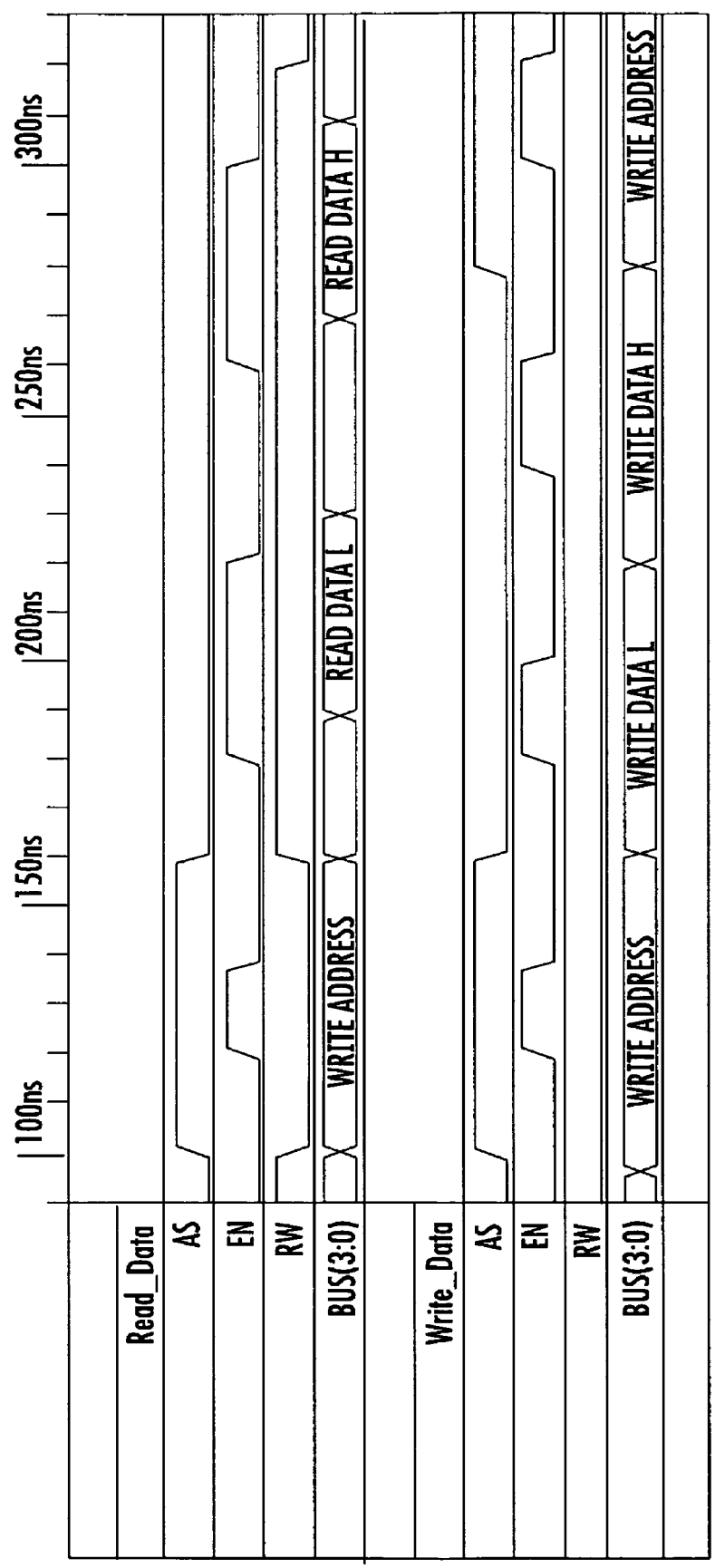
FIG. 15 is a timing diagram for the microprocessor and Complex Programmable Logic Device (CPLD) shown in FIG. 14.

FIG. 15 shows the timing to read and write data from microprocessor 440 to CPLD 416. Registers in the CPLD are assumed to be 8 bits (or two nybbles), so there are two reads or two writes for each data cycle. The signal PB_RS_AS is used for the CPLD interface as the address select. The data bus, PB_D[3:0], has the register address when AS is high and the read or write data when AS is low. The address cycle is always a write from the microprocessor to the CPLD. The data cycle direction is determined by the PB_RW signal with active high as a read cycle.

The 16 CPLD 416 registers are 8 bits, though not all the registers are used. Table 5 lists the registers in the CPLD and the tables 6-12 describe the register bits.

TABLE 4

Programming table for headphone amplifier MAX9850.

| Register Address | Function | B7 | B6 | B5 | B4 | B3 | B2 | B1 | B0 |
|---|---|---|---|---|---|---|---|---|---|
| 0x2 | Volume | Mute | Slew | VOL(5:0) | | | | | |
| | | 0 | 1 | 0x00 | | | | | |
| 0x3 | General Purpose | GM(1:0) 0x2 | | GPD GPIO Output | DBDEL(1:0) Debounce Delay 0x01 | | Mono | | ZDEN Zero Crossing |
| | | | | 1 | | | 0 | 0 | 1 |
| 0x4 | Interrupt Enable | | ISGPIO Allow alerts | ICLK PLL Lock | ISHPS Headphone Detect | IVMN Minimum Volume | | | IICH Overload |
| | | | 0 | 1 | 1 | 0 | 0 | 0 | 1 |
| 0x5 | Enable | SHDN* Power On | MCLKEN DAC En | CPEN(1:0) Charge Pump 0x3 | | HPEN Headphone output | LNOEN Line On | LNIEN Line In | DACEN DAC En |
| | | 1 | 1 | | | 1 | 1 | 0 | 1 |
| 0x6 | Clock | | | | | IC(1:0) Internal Clock Divide | | | |
| | | 0 | 0 | 0 | 0 | 0x0 | | 0 | 0 |
| 0x7 | Charge Pump | SR Slew Rate (1:0) 0x2 | | 0 | | CP(4:0) Charge pump divider 0x09 | | | |
| 0x8 | LRCLK MSB | INT Integer/Float 0 | | | | MSB (14:8) RLCLK divider 0x0 | | | |
| 0x9 | LRCLK LSB | | | | | LSB (7:0) RLCLK divider 0x0 | | | |
| 0xA | Digital Audio | MAS Master | INV Channel Order | BCINV Falling Edge Latch | LSF LSB first | DLY Second Rising Edge | RTJ Right Justified | WS(1:0) Word Size 0x0 (16 bits) | |
| | | 0 | 0 | 0 | 0 | 1 | 0 | | |

Two LCD displays 320 and 324 are interfaced from microprocessor 400 via the "Parallel Bus" or PB_pins shown in the PIO table. The two enable signals PB_EN_LCD1 and PB_EN_LCD2 select the respective LCD. The signal PB_RS_ AS is used for the LCD interface as the register select (RS) control.

Power Management board 430 consists of three major functions: (1) Battery Charger and Monitor 460, (2) Multiple Source Power Controller 462 and (3) Motor power shutoff 464. Multiple Source Power Controller 462 switches between the DC voltage from the power supply (18V nominal) and the battery source. The Two-wire interface connects to battery 432.

CPLD 416 has the watchdog alarm logic and the panel switch inputs. This interface uses the "Parallel Bus" (or PB_) which is shared with the LCD interface. Other hardware signals pass through the CPLD to provide a path to the microprocessor such as the ready signal from the ADC 414.

TABLE 5

CPLD Registers List

| Register Mnemonic | Purpose | Read or Write | Address (hex) |
|---|---|---|---|
| CpldId | CPLD Identification code == 0x51 | R | 0 |
| CpldRev | CPLD Revision code | R | 1 |
| Diagnostic | Diagnostic Register | RW | 2 |
| WatchdogPet | Watchdog pet register | RW | 3 |
| Status | Status Register | R | 4 |
| Control | Control Register | W | 5 |
| SwitchesL | Panel Switches 7:0 | R | 6 |
| SwitchesH | Panel Switches 15:8 | R | 7 |
| MotorSpeedL | Motor Speed bits 7:0 | R | 8 |
| MotorSpeedH | Motor Speed bits 15:8 | R | 9 |
| | Note: MotorSpeed is a 16 bit signed number for motor speed in units of RPM. | | |

TABLE 5-continued

CPLD Registers List

| Register Mnemonic | Purpose | Read or Write | Address (hex) |
|---|---|---|---|
| | | | A |
| | | | B |
| | | | ... |
| | | | F |

TABLE 6

CpldId and CpldRev Register Format

| 7:0 |
|---|
| ID[7:0] or Rev[7:0] |

ID is the identification code of the DSP board, CPLD=TBD fixed. Rev is the revision code for the DSP board CPLD.

TABLE 7

Diagnostic Register

| 7 | 6 | 5 | 4 | 3 | 2 | 1 | 0 |
|---|---|---|---|---|---|---|---|
| 0 | 0 | 0 | 0 | Hdr3 | Hdr2 | Hdr1 | hdr0 |

Hdr[3:0] is the input from the four head lines on the board. Output (writes) to register are ignored.

TABLE 8

Status Register

| Bit | Mnemonic | Description |
|---|---|---|
| 7 | POWER_FAILURE# | Power Failure. Also, goes to the FIQ (PA19) line of uP. When first goes low the uP power has 50 ms complete all tasks before losing power. |
| 6 | LOW_BATTERY | LOBAT signal from the LT1479 |
| 5 | DC_IN_GOOD | DC Power from the power supply is good. When this flag is low the DC power is off and therefore the uP must be powered from the battery. |
| 4 | 0 | |
| 3 | MtrPwrFdbk | Motor Power Feedback. Indicates motor power state on the PM board. (Used with watchdog test.) |
| 2 | PumpDoorOpen | Pump door is open flag |
| 1 | wdOut | Watchdog output |
| 0 | AirDetectorIn | Air Detector Input line (1 = air or air-bubbles; 0 = liquid only) |

TABLE 9

Control Register

| Bit | Mnemonic | Description |
|---|---|---|
| 7 | Enable_piezo | Enable piezo alarm device to sound when watchdog times out. |
| 6 | | |
| 5 | BATTERY_OFF | Disconnect the battery under SW control. Used when the power supply off (DCIN off). uP power goes off after setting this control bit. |
| 4 | DCIN_BAT# | Select power from the DC power supply when high, from the battery when low. This may be done automatically by the hardware if user disconnects AC power (DC_IN_GOOD=0). |

TABLE 9-continued

Control Register

| Bit | Mnemonic | Description |
|---|---|---|
| 3 | CLED2 | CPLD diagnostic LED #2 |
| 2 | CLED1 | CPLD diagnostic LED #1 |
| 1 | | |
| 0 | AirDetectorTest | Air Detector test output. Runs test when in set high when liquid is present. Software should turn bit off after setting. Signal is active low (test runs when low). |

TABLE 10

Watchdog Register

| 3 | 2 | 1 | 0 | 3 | 2 | 1 | 0 |
|---|---|---|---|---|---|---|---|
| 0 | 1 | 1 | 1 | 0 | 1 | 0 | 1 | wdec[3:0] is Write a 0x75 to "pet" the watchdog. No other value is valid.

TABLE 11

SwitchesL, Panel Switches 7:0

| Bit | Mnemonic | Function |
|---|---|---|
| 7 | SW8 | CLEAR |
| 6 | SW7 | PRIME |
| 5 | SW6 | SCROLL |
| 4 | SW5 | (Upper Center) |
| 3 | SW4 | ACCEPT |
| 2 | SW3 | MENU |
| 1 | SW2 | ADVANCE |
| 0 | SW1 | BOLUS |

TABLE 12

SwitchesH, Panel Switches 15:8

| Bit | Mnemonic | Function |
|---|---|---|
| 7 | SW16 | Not used = low |
| 6 | SW15 | Not used = low |
| 5 | SW14 | SILENCE |
| 4 | SW13 | RUN/STOP |
| 3 | SW12 | DOWN ARROW |
| 2 | SW11 | PAUSE |
| 1 | SW10 | UP ARROW |
| 0 | SW9 | (Upper Right) |

Exemplary Microprocessor Programming

One example of suitable programming for processor or controller 400 is set forth in a computer program listing appendix which is submitted on a single compact disc, and which is incorporated herein by reference.

Air Bubble and Pressure Detection and Hydration Settings

Control subsystem 34", FIG. 3 may also include electronic air detector 86 that prevents infusion of air into the patient. The air detector 86 is of ultrasonic type and can detect air in amounts exceeding approximately 50 micro liters traveling inside the infusion tubing 32. In one example, air detector 86 employs technology based on the difference of the speed of sound in liquid and in gaseous media. If an air bubble is detected, the pump 22' can be stopped almost instantaneously.

The controller software reads the bubble detector output and is programmed to generate an alarm signal whenever the pump is running and bubbles are detected for more than 540 ms in an 8 minute window. The bubble detector will detect a 50 µl bubble and generate a minimum pulse of 11 ms.

On power up, the controller software may query the user to select new patient or same patient using the menus and keys discussed with reference to FIG. 13. If the same patient is selected, the controller software may restore the system settings and control values to resume operation before power was turned off.

If a new patient is selected, the software may clear the control values (such as accumulated infusion accumulated urine, bolus delivered) for the new patient. System settings are restored to their default values. The system settings that are restored from PROM to CPU memory to their default values are Bolus Amount Setting, Net Gain Settings, Maximum Hydration Settings, and Minimum Urine Setting.

Upon detection of low power condition, the software may store the system settings and other control parameters, needed to restore operation on the same patient, in non-volatile memory (PROM such as an EEPROM).

A pressure sensor may also be incorporated to measure pressure in the infusion line downstream of pump 22', FIG. 3 and upstream the patient I.V. The software may read the pressure sensor to detect occlusions. If the pressure exceeds 15 psi for 30 seconds, for example, the controller software may report an alarm condition. If the pressure exceeds, for example, 25 psi at any time, or 10 psi for longer than one minute, the software may report an alarm condition. Meanwhile, the controller software may slow down or stop the pump for a short time to allow the occlusion to be resolved on its own before alarming the user. The software may detect when the Maximum Hydration Limit (set by the user) is reached. In run mode, the software may generate an alert if the cumulative net gain (hydration) exceeds the maximum hydration limit and stop net gain infusion but continue urine balancing. The software may allow the user to override this condition by increasing or decreasing the net gain setting at any time via the user interface.

In run mode, the software may generate an alert if the measured urine over a 30 minute period is less than the minimum urine output setting. The setting can be chosen by user, for example from 0 to 500 ml/hour. The infusion fluid weight is used to enhance accuracy of fluid delivery over time. Reduction of weight in the bag is continuously monitored in addition to the pump speed to ensure redundancy, added accuracy, and to inform the user in advance that the fluid bag is almost empty.

The urine weight output displays urine volume and urine output rate and enables automatic replacement of fluid lost in urine. The controller software measures urine weight as described herein and adjusts the pump speed to add the amount lost in urine to the Net Hydration Gain setting and Bolus Setting set by the user.

Weight measurements can be collected by software every 100 milliseconds. The following software algorithms are applied to the weight scale measurements.

The infusion weight scale reading is filtered with a 10 second moving average filter. The infusion weight scale is considered to be stable: if half of the samples are within ±16 g of the previous filtered value, or if the difference between the minimum weight reading and the maximum weight reading in the filter window is less than 16 g.

The infusion weight scale may be declared unstable if it does not meet the stable criteria (defined above) for 15 seconds. The urine weight scale reading is filtered with a 60 second moving average filter. The urine weight scale is considered to be stable if half the samples are within ±100 g of the previous filtered value, or if the difference between the minimum weight reading and the maximum weight reading in the filter window is less than 100 g.

The urine weight scale may be declared unstable if it does not meet the stable criteria (defined above) for 60 seconds. If the weight scale is not stable, the system switches to the PAUSE (KVO) and alerts the user.

If a weight scale (hydration or urine) is not stable, the system switches to the PAUSE (KVO) and alerts the user. KVO means that no urine volume is replaced, hydration flow is reduced to value sufficient to prevent vein from closing (KVO-Keep Vein Open) and to maintain baseline or minimum hydration. The user has an option to CLEAR or cancel the condition and the infusion amount equal to the amount of urine accumulated during PAUSE will be infused into the patient by software algorithm. The later will only occur if the weights scales are now reliable and stable. In FIG. 9B, the abnormal hydration fluid measurement is indicative of a replacement of the source of hydration fluid and the corrective action taken by the controller software is the generation of an alarm signal.

The following additional functions may be embodied by the software using data from the weight scales.

During the run mode, the software compares the amount of volume delivered as determined by the pump rate against the amount of volume delivered as determined by the weight change of the hydration fluid bag scale. If this difference over a 15 minute period is greater than 50% or 25 ml, then the software generates an alarm. During infusion, if the 2 liter urine bag measures, for example, more than 1.8 kg, the software shall generate an alert. During infusion, if the software measures the standard one liter hydration bag weight to be less than 50 g (almost empty) or if the software measures the difference between the initial hydration bag weight and the current bag weight to be greater than 950 g, it can generate an alarm.

In run mode, the software can generate an alert and go to pause mode if the measured urine drops more than 50 g over a 5 minute period. There should not be sudden drops of urine weight. This may indicate opened valve or disconnected or opened tube.

In run mode, the software may generate an alert and go to pause mode if the measure urine increases more than 500 g over a 5 minute period. This is an unlikely "physiologic" event and is identified as hardware failure or user misuse such as inadvertently placing additional tension or weight on the hook.

Urine bag 52, FIG. 9 may also include a label instructing the nurse to push pause on controller console 82, FIG. 3 before emptying the urine bag. The function of the pause button is explained with reference to FIG. 13.

One Prototype System

Figure 16:
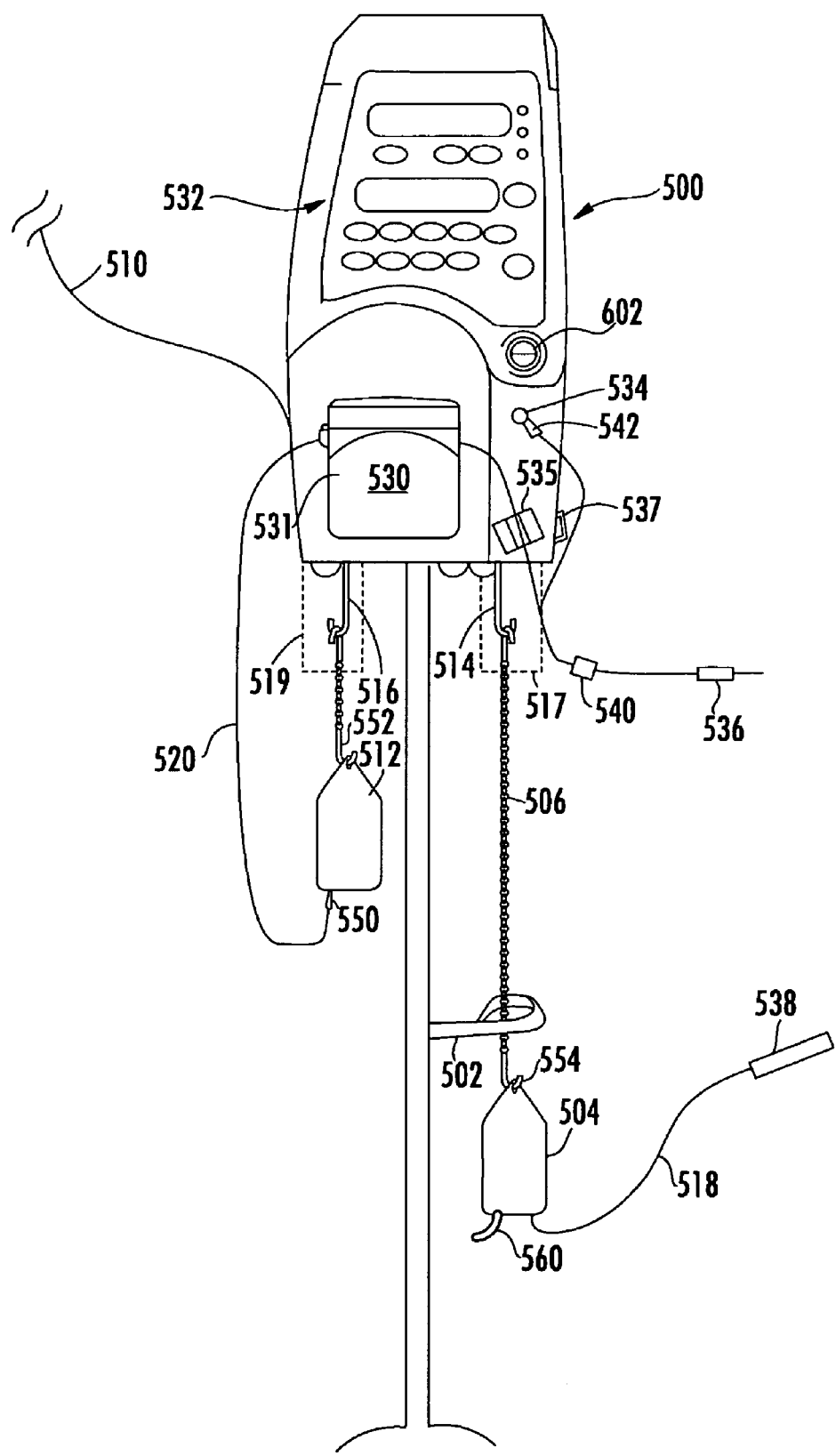
FIG. 16 is a schematic front view of a prototype balanced hydration unit in accordance with the subject invention.

One prototype system includes console 500, FIG. 16 and infusion and urine collection sets. Motion restraining clamp 502 is for urine bag 504 chain 506. The integrated infusion set includes an IV bag spike, a Luer-to-Foley connector for priming, and a urine collection set includes an integrated urine bag. The power requirements are 115/220 VAC, 60/50 Hz, 25 VA. An auxiliary ground post (potential equalization) for the device is on the rear of the case (not shown). An RS 232 port is also provided. When mounted on an I.V. Pole, the system requires an area of approximately 20×20 inches. Console 500 is placed on the pole so that the urine collection bag 504 is above floor level and not touching the floor or other equipment. Urine collection bag chain 506 is passed through motion restrictor ring 502 to prevent excessive swinging of the bag. Urine collection bag 504 is below the level of patient to facilitate urine drainage, and urine 504 and hydration fluid 512 bags are hanging freely on hooks 514 and 516, respectively, and not supported or impeded. Protection tubes 517 and 519 shown in phantom may be provided about hooks 514 and 516. The urine 518 and hydration 520 tubing should not kinked or pinched, and should not pull or strain the weight measuring devices.

The system maintains hydration balance by measuring patient urine output and infusing hydration fluid (prescribed by physician) into the patient I.V. to balance the fluid lost in urine. In addition to urine volume replacement, the system implements a user-set net fluid gain. Net fluid gain is defined as the amount of fluid in ml/hour infused into I.V. in addition to the replaced volume of urine. The system also allows rapid infusion of a Bolus of fluid at the user request. The amount of Bolus can be selected by user and typically the bolus is infused over 30 minutes. Bolus is infused in addition to the Net Fluid Gain and the replaced volume of urine. Console 500 includes a microcontroller device that has means for measuring urine and the ability to infuse hydration fluid into the patient. The infusion set allows the console to pump fluid from a hydration fluid bag to the patient at a controlled rate. The disposable urine collection set collects the patient's urine to allow it to be measured accurately. Console 500 is also equipped with an internal battery that can sustain operation in the event of power outage or during short periods of time, for example, when the patient is moved. Console 500 includes roller pump 530, user interface 532, two weighing scales (not shown), air detector 535, post-pump pressure sensor 534, an electrical connector for AC power, and mechanical interfaces for holding the set in place. Console 500 controls the rate at which fluid is infused and monitors urine volume by weight measurement.

Figure 17:
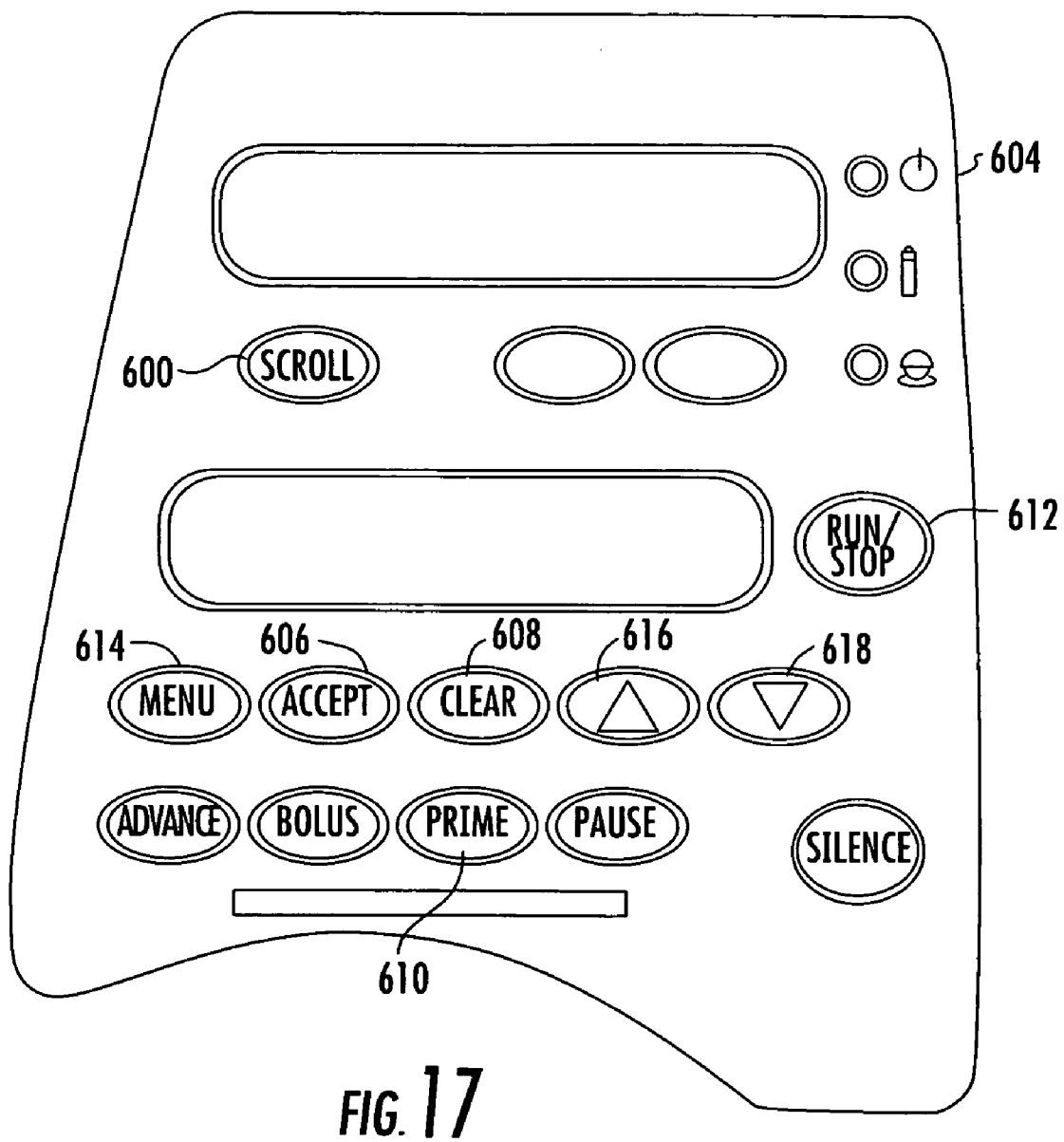
FIG. 17 is a schematic front view of a portion of the user interface for the unit shown in FIG. 16.

To initiate treatment, the system requires: a) peripheral I.V. access 536, b) a urinary Foley catheter 538 and c) an appropriate number of one liter bags with the physician prescribed hydration fluid. The set is automatically primed by console 500. During the operation, the user is responsible for a) draining the urine bag when full, b) replacing hydration fluid bags when empty, and c) responding to alarms and alerts issued by the system. Interface 532 can display four lines of text at a time. The system automatically scrolls through the system parameter display items. Each item is displayed for 5 seconds. The user can scroll to the next system parameter display item by pressing scroll key 600, FIG. 17. Depending on the system condition and operating mode, the following parameters are displayed: the net fluid gain accumulated since the start of the therapy in ml, the total fluid infused since the start of the therapy in ml, the total urine collected since the start of the therapy in ml, the urine rate averaged over the last 15 minutes in ml/hour, if bolus delivery is in progress, the system displays amount of time remaining to complete bolus delivery, the operating mode (Run, Pause or Stopped), and the total therapy time. The software also displays the source of power (DC or battery), the amount of estimated battery life in minutes and the state of battery charge in percent. Alert or alarm messages, if such a condition exists, are also displayed. The system allows the user to enter following parameters: desired Net Fluid Gain in ml/hour, Bolus Amount in ml, maximum allowed accumulated Net Fluid Gain in ml, and minimum urine output in ml/hour for alert only.

The system also includes the following features designed to protect the patient from potentially hazardous conditions and malfunctions and alarm the user as needed. An air detector 535 with automatic infusion pump 530 shut-off, post-pump downstream pressure sensor 534 to detect occlusions, and pump motor speed monitoring by an optical encoder, weight scale monitoring of infusion fluid to detect leaks and pre-pump upstream occlusions, weight scale monitoring of urine volume to detect leaks and urine collection set occlusions, free flow protection device 540 (pressure valve), and a pump door open detector with automatic motor shut off, critical components of these safety circuits are tested automatically prior to each therapy. Some components are monitored for integrity continuously during therapy.

To initiate treatment, medical grade power cord 510 is connected to the power plug receptacle on the rear of the device. The device is then plugged into a grounded electrical outlet. The "POWER ON/OFF" key 602, FIG. 17 on the front panel is then pressed. A short tone indicates the diagnostic self-test is starting. The message "Power on Self Test In Progress" is displayed. The device progresses through the test for approximately 30 seconds. Confirm that the AC MAINS symbol 604 located on the front panel is illuminated. If the self-test terminates with an audible alarm and an error message on the display, make a note of the error code displayed. If error cannot be corrected, press the POWER ON/OFF key, wait 5 seconds, and then repress the "POWER ON/OFF" key as above. The System progresses to the Same Disposable Set, New Disposable Set. The following message is displayed "Press ACCEPT 606 for Same Patient or CLEAR 608 for New". Pressing the ACCEPT KEY restores all the parameters used for therapy before power was turned off including Therapy settings including Bolus administration and Net Gain target, and Therapy parameters such as elapsed time, urine made and fluid infused. Pressing CLEAR KEY 608 indicates that the new infusion set is used on the same patient or that a new patient therapy is started. All settings and parameters are restored to zero or system defaults. Before therapy is started the System shall be PRIMED. Priming procedure requires loading and setting of disposables. Proceed as follows to load the INFUSION SET tubing onto the console. Visually examine the package to determine that the package has not been opened or damaged during shipping. Open the package. Release the ties holding the set to the packing card. Carefully remove the INFUSION SET from the packaging. Use the I.V. pole to hang the set while preparing to load. Preserve sterility. Air detector 535 is connected downstream of the pressure sensor. Start by connecting the infusion line air hydrophobic filter 542 to pressure transducer connector 534 on the front of the console. Use a gentle but firm turning motion until it stops. Open the pump door 531 and load the pump segment tubing over the rollers. Assure that the clips on ends of the raceway are lined up with the tube segment. Close the pump door firmly until a click is heard. Check that the tubing is aligned correctly. When the pump door is open the pump is stopped and can not move. Spike a hydration bag 512 with the IV Set spike using standard technique. Ensure that the drip chamber 550 is at least 50% full by gently squeezing and releasing the chamber. Hang the full 1 liter hydration fluid bag on the left chain hook 552 of the console. Ensure free swinging motion of the bag. The system is designed for use with 1 (one) LITER infusion bags only. Do not use any other bag sizes. Load the infusion set tubing segment immediately to the right of the pressure sensor into air detector 535. Assure that the tubing is firmly seated at the bottom of the air detector channel. Use stretching or flossing motion to set the tube in the slot. Handle 537 may be provided to seat the tubing in sensor 535. The system is equipped with the sensitive (50 micro liter) ultrasonic air detector. If tubing is not loaded into the detector properly, the System will not operate. Hang the empty urine collection bag 504 on the right chain hook 554 of the console. Ensure free swinging motion of the bag. Ensure that the chain 506 of the urine bag is passed through retainer clamp 502. The retainer clamp will prevent excessive swinging of the urine bag. Ensure that the bag is hanging unobstructed and unsupported to assure proper weight measurements. Check to see that the drain valve 560 at the bottom of the urine collection bag 504 is fully closed. If not, you should close the valve. Connect a luer connector (normally used for I.V.) on patient end of the infusion set to the foley catheter adapter on the patient end of the urine collection set tubing. Use the Foley-to-luer adaptor to make the connection. This adapter is intended for priming only and is discarded before patient use. Use the I.V. pole to support the length of tubing. Ensure that tension is not exerted on the bags and the bag suspension system. Make sure the clamps on the withdrawal and infusion tubing are open. Press the PRIME button 610 and Press the ACCEPT key 606 to start priming the INFUSION SET. The pump will run and stop independently for approximately 3 minutes. Approximately 150 ml of fluid will be pumped from the hydration bag 512 into the urine collection bag 504. While the pump is running, the user may tap gently on the tubing and/or squeeze the drip chamber to release any bubbles. The user should also inspect the infusion set for any leaks during priming. The user can discontinue priming by pressing the stop key 612. When the pumps stop, the user may carefully examine the entire infusion set and the filter to assure it fully primed and that no air is present in the blood tubing. If no air is present, the user may proceed to initiating therapy. If any alarm occurs during priming, refer to the Alarm Section of this manual for more detailed help in correction of these alarms. Once the problem has been corrected, the user should re-prime the infusion set prior to initiating therapy. At the end of automatic priming the System will display message: "Check Weight Bags. Don't Touch Bags." It is important not to interfere with the bag suspension system at this time. Disconnect the INFUSION SET I.V. connector from Foley Connector of the Urine Collection Set. Remove and discard the Luer-To-Foley adapter. The user may close the pinch clamp on the infusion line to prevent fluid leakage. Connect the infusion set connector to the already inserted I.V. access device. Assure that no air enters the system. Turn the connector until it clicks closed. Close the pinch clamp the urine collection tubing prevent fluid leakage. Connect the urine tubing connector from the urine collection bag to the Foley catheter. Assure the connection does not leak. Press the run button 612 to start therapy. The system has three user settable parameters: Net Gain Setting, Maximum Hydration Setting, and Minimum Urine Output Setting. All of these parameters can be viewed and changed using the MENU Key 614. Parameters are changed by selecting from the scrolled list using UP and DOWN Arrow keys 616 and 618. To change the parameter to selection the user needs to press the ACCEPT Key 606. If the user does not press the accept key shortly after making the selection, the screen is cleared, the new value is rejected and the system continues with the current value. New parameters are implemented only after the ACCEPT key is pressed. This value is the amount of hydration (in ml/hour) that the patient will receive IN ADDITION to the replacement of urine volume. The net gain is selectable from 0 to 500 ml/hr in increments of 25 ml. This setting can be changed at any time during therapy using the MENU key selection 614 and the UP and DOWN Arrow keys. The FLUID BOLUS is given to the patient is in addition to NET GAIN amount. Default NET GAIN is set to ZERO when the New Patient Therapy is selected. This value is the maximum total amount of NET GAIN hydration (in ml/hour) that the patient will receive IN ADDITION to the replacement of urine volume. The value for maximum hydration is selectable from 0 to 1,500 ml in increments of 100 ml. This setting can be changed at any time during therapy using the MENU key selection and UP and DOWN Arrow keys. After this value is reached, only urine volume replacement will occur (net zero replacement). The user is notified by an alert that this level is reached. This number sets the minimum desired urine output level. This setting does not affect the System performance. If the urine output is consistently below the set value user is notified by an alert sound and a display message "Minimum Urine Level Not Reached". The minimum urine output setting shall be selectable from 0 to 150 ml/hr in increments of 50 ml/hr using UP and DOWN Arrow keys. The System is designed to stop automatically and alarm when the Hydration fluid bag is almost empty (or with approximately 50 ml of fluid remaining in the bag). Hydration fluid bags can be also changed at any time by pushing the STOP button and stopping the pump. If user desires to replace bag that is not empty, user shall push STOP button to avoid air in the circuit. If the bag reaches the minimum acceptable volume, the System will be stopped. The message "Saline Bag Empty. Replace Saline Bag" will be displayed and alarm sound. The alarm can be silenced using SILENCE button for 2 min. To continue the operation press CLEAR button. The bag is replace using standard technique common to all I.V. sets with high flow drip chambers. After the bag is replaced, therapy can be restarted by pushing the RUN button. System will automatically account for the change of weight. The system will automatically replace fluid lost by patient in urine while the pump was stopped. This may result in temporary high infusion rate. If the urine bag is full, the system will automatically switch to PAUSE mode. In the PAUSE mode, the system will issue an alert and stop urine volume replacement. To maintain patency of the venous access, hydration will continue but only at a pump flow of 70 ml/hour. The user can empty the bag when full or at any time if desired by the user. The urine collection bag may emptied by performing the following steps. The system is designed to alarm the user when the urine collection bag is almost full. Urine bag holds 2 liters of urine. The system will display message: "Urine Bag Full, Empty Urine Bag". Push the PAUSE KEY to switch to Pause Mode. Note the total volume in the urine collection bag. Record it appropriately.

It is the responsibility of the user to push PAUSE button before draining the urine bag. Failure to do so, draining bag during without Pausing the System Operation may result in incorrect measurement and display of urine volume and alarms. Open the drain valve at the bottom of the URINE COLLECTION BAG COUNTERCLOCKWISE and drain into a container. It is recommended that the user drain the urine into a marked container and record that value prior to discarding the urine. When in PAUSE mode, the system will not replace fluid lost in urine. It is user responsibility to push the PAUSE or RUN button to restart automatic urine volume replacement. Therapy will not restart automatically until PAUSE or RUN button is pushed. Close the urine bag valve. PUSH PAUSE KEY to switch back to RUN mode. Do not leave system in the Pause mode unless intended. The user may empty the urine collection bag prior to it being full. Thus, the total number of times the bag was emptied may overestimate the total fluid removed. The BOLUS Button allows the user to infuse additional fluid into I.V. when clinically indicated. The volume set for the BOLUS is always delivered over 30 minutes. BOLUS Key can be only used when the device is running. If the device is PAUSED or STOPPED, a bolus cannot be initiated. Push BOLUS key. The system will display the BOLUS AMOUNT SELECTION Menu. Select bolus amount from 0-250 ml in increments of 50 ml using Navigation Keys. Push ACCEPT Key to confirm the selection. The bolus amount will be delivered over 30 minutes in addition to the user set Net Gain and Machine Set Urine Volume Replacement. During the BOLUS delivery the System will display the "Bolus Remaining" volume and bolus "Time Remaining" information automatically. Bolus Volume is infused in addition to the user set NET GAIN and the replaced URINE VOLUME. If the BOLUS is interrupted by user PAUSE or the System being STOPPED by the user, BOLUS delivery will be completed as soon as the system returns to normal operation. The Advance and Pause Keys help user perform maneuvers frequently encountered in I.V. Hydration therapy. The pause mode is similar to the KVO (Keep Vein Open) mode frequently used in I.V. therapy. It is intended to disable urine volume monitoring and replacement when the urine bag is drained or when the patient is moved or urine drainage is re-arranged. Press and HOLD the ADVANCE KEY to displace fluid and air though the INFUSION SET. Releasing the ADVANCE KEY will stop the pump in 2 seconds. If the ADVANCE KEY is held continuously for longer than 30 seconds the pump will automatically stop. Releasing and pressing and holding the key again will allow pump to run for additional 30 seconds.

Air detection is disabled during ADVANCE KEY operation. It is the user's responsibility to prevent the infusion of air into the patient. The software stops the urine volume replacement control when the user presses the pause key and the system is in run mode. The user may drain the urine bag during this mode. The software shall resume operation when the user presses the PAUSE key and the system is in pause mode. The system runs the pump at a rate of 70 ml/hr to keep the vein open and maintain I.V. hydration. During pause mode, the system generates a low volume beeping. After 15 minutes, the System will increase the volume to high to bring to user's attention that the patient is not receiving urine volume replacement. Upon exit from Pause mode and into run mode, the System adapts to the infusion and urine bag weight changes to correctly resume hydration control. When the FMS System is PAUSED, the Urine volume is not being replaced. Infusion is set to 70 ml/hour, until the user terminates the PAUSE. Silencing and Clearing an Alarm may not eliminate the Alarm cause. Carefully investigate and correct all Alarms and Alerts.

The alarms generated by the FMS System indicate the presence and severity of the alarm. The lighted LED and type of sound represent the general level of importance of the current operating conditions to the user. Press the SILENCE key to silence the alarm for 2 minutes while performing corrective actions. Respond to the information displayed on the screen and correct the conditions that caused the ALARM.

Press the CLEAR Key to reset the alarm. If the FMS-1 is still in RUN Mode and the alarm condition is still present, the ALARM will re-annunciate. If the FMS-1 is in STOP Mode, the Alarm condition may be cleared but may re-annunciate if the condition has not been removed when the system is restarted. Some Alarms such as System Malfunction Alarms can not be cleared or silenced unless Power is turned OFF and ON. Depending on the cause of an Alarm or Alert System may respond in two ways: alarm the user and stop the pump (for example if Air is detected or hydration fluid bag is empty) and alarm the user and stop urine volume replacement while maintaining pump flow at 70 ml/hour (as for example if urine bag is full).

While the system will provide information on the most likely causes of the alarm, the user must exercise caution and examine all possible options if the information displayed does not solve the problem.

The user can select the maximum net gain for single patient THERAPY from 0 to 1,500 ml. When this maximum net gain is reached, the system generates an alert. Without user intervention further net gain is not added to the urine volume replacement, patient therapy is "net zero" balance. The user can override this condition by increasing the net gain setting at any time. Clear the alarm if no further Net Gain is desired or change the Maximum Net Gain Setting.

The minimum urine not reached alert is designed to inform the user that over the period of 30 minutes patient's urine output was below user selected minimum level. This Alert does not affect the System operation and intended to provide information to enable the user to make clinical decisions. User can choose to Clear the Alarm, Change the setting or Silence this alarm. The air detected alarm significant amount of air is detected by the ultrasonic air detection. The infusion pump is stopped immediately until user corrective action. This alarm can be caused by air entrained from the damaged or disconnected tubing, air entrained from the drip chamber, or a tube dislodged from the air detector slot. Recommended action includes a check of Leaks and Drip Chamber level, Use of the advance Mode to remove/aspirate air bubble, or a restart of therapy by pressing RUN key after removing the air.

If an Infusion Set Occlusion Alert is generated, the pressure sensor has detected a downstream occlusion of the infusion Line. The Infusion pump is stopped immediately until user corrective action. This alarm can be caused by closed clamp, a kinked tube, or an occluded I.V. Recommended Action includes a check of the clamps, a check of the tubing, or flushing the I.V. following the accepted clinical technique.

The Urine Bag Full Alert indicates the system has detected that the Urine Bag is full using the weight scale. Hydration continues at NET GAIN RATE or 70 ml/hr, which ever is higher. Urine volume replacement is disabled during this time. After the urine is drained, therapy will be restarted as before the alert. Recommended Actions include checking the urine bag level, pressing the PAUSE key, draining the urine bag using accepted clinical technique, and push PAUSE key again.

The Fluid Bag Empty Alert indicates the system has detected that the Hydration Fluid Bag is almost empty. There can be approximately 50 ml of fluid left in the bag. System automatically STOPS the hydration pump. Recommended Actions include checking fluid bag level, replacing the bag using accepted clinical technique, and pushing the RUN key.

If there is a less than 10 minutes battery life remaining and the system is powered from battery, the System generates an alert with a low volume and displays message "Battery Low". If there is a less than 2 minutes battery life remaining and the system is powered from battery, the software generates an alarm with a high volume and display message "Battery Critically Low, Connect AC now".

The system monitors urine weight for abrupt increase that can not be explained by normal urine output. If an abrupt increase of urine weight is detected an Excessive Urine Weight Increase Alert message is issued to the user. The system is automatically switched to PAUSE mode. Hydration continues at 70 ml/hr. Urine volume replacement is disabled during this time. User can CLEAR the alert and therapy will be restarted as before the alert. This alarm can be caused by an object pulling on the urine scale hook, additional weight added to urine bag, or a hardware malfunction. Recommended Actions include ensuring that Urine collection bag is freely hanging on the right side hook, clearing the Alert, and push PAUSE key after correcting the condition.

The system monitors urine bag for sudden decrease of weight. If such decrease occurs during therapy a Urine Bag Leak Alert is issued. This alarm can be caused by the user draining urine without pushing the PAUSE Key, and/or a leak from the bag. Recommended Action includes checking for leaks and checking the tubing.

The system relies on weight scales to determine urine output and fluid replacement rate. If the device is excessively bumped the weight scale readings can become erratic and unreliable. The System automatically detects such conditions and issues an Unstable Scales Alert. If the weight scale is not stable, the system enters the PAUSE mode automatically. Whenever System is in the PAUSE Mode, urine volume is not being replaced. The patient receives 70 ml/hour. When in the PAUSE mode, the System will beep at a low rate and volume. After 15 minutes, the System will increase the volume to high to bring to user's attention that the patient is receiving only the KVO rate of hydration. Recommended Action includes bringing the system to rest and push PAUSE key to restart balancing. During patient hydration System monitors the weight of the hydration fluid bag and compares it to the pump flow rate. If serious mismatch is detected an Infusion Weight Mismatch Alert is issued and the Pump is stopped. This alarm can be caused by a disconnected tube, a kinked tube or other kind of Pre-Pump occlusion, or a leaky bag or tube. Recommended Action includes checking for leaks, checking for occlusion, and a restart therapy if the condition is corrected by pushing RUN key.

If the Pump Door is opened while pump is running, the system generates low volume beep and displays a Pump Door Open Alert message. If the pump door is opened when the system pump is not running, a message indicating that pump door is open will be displayed. Whenever the pump door is opened, the pump rollers will not move and pump will not RUN.

A Prime Test Failure alert may occur at the end of priming. The system checks a) the performance of the weight scales by comparing them to each other, b) the pressure Sensor, and c) the air detector. If this test does not pass, patient therapy will not be allowed. Following message is displayed "Prime Test Failed" followed by the failed component (i.e. weight scale, pressure sensor or air detector). This alarm can be caused by hardware failure, the user interfering with weight scale measurement, incorrect connection of fluid path during priming, bags not on hooks, a tube not in air detector, or a disconnected pressure sensor tube. Recommended actions include ensuring that the infusion set is connected to the Urine Collection bag and fluid is pumped from former to later, ensuring that urine collection bag is freely hanging on the right side hook and the hydration fluid bag is freely hanging on the left side hook, ensure the proper connection of pressure and air sensors, and repeating the procedure using the PRIME key.

System malfunctions result from internal system diagnostic tests continuously executed by the system when in operation. They typically indicate a possibility of a component malfunction. An alarm is issued and the system is stopped. System malfunctions, in most cases can not be cleared. User is advised to turn power off and on once. If the system malfunction condition remains, the system should not be used.

Although specific features of the invention are shown in some drawings and not in others, this is for convenience only as each feature may be combined with any or all of the other features in accordance with the invention. For example, there are other ways to determine a patient's urine output and other ways to quantify the amount of hydration fluid administered to the patient. There are also other ways to redundantly check the amount of hydration fluid administered the patient. Also, the words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A patient hydration system comprising:
an infusion subsystem including a pump which infuses an infusion fluid into a patient;
a urine output measurement subsystem which measures urine output by the patient and including a urine collection chamber for collecting the urine output by the patient;
a console including an input for setting a desired fluid balance, the console further including a priming input;
a controller associated with the console and responsive to the urine output measurement subsystem and including a balancing function which controls the infusion subsystem to administer infusion fluid into the patient based on the input desired fluid balance and the amount of urine output by the patient; and
a priming adapter configured to connect the infusion subsystem to the urine output measurement subsystem;
the controller configured, in response to the priming input, to automatically control the pump to drive infusion fluid from the infusion subsystem through the priming adapter and into the urine collection chamber to test the operation of the infusion subsystem and the urine output measurement subsystem and to verify the amount of infusion fluid pumped matches the amount of infusion fluid entering the urine collection chamber within a predetermined range.

2. The system of claim 1 in which the controller is configured to test the operation of the infusion subsystem and the urine output measurement subsystem in response to the priming input by weighing the urine collection chamber.

3. The system of claim 1 in which the controller is configured, in response to the priming input, to control the infusion subsystem to drive at least 150 mL of infusion fluid into the urine output measurement subsystem.

4. The system of claim 1 in which the controller is programmed to determine and display on the console the amount of infusion fluid infused into the patient and an amount of urine output by the patient.

5. The system of claim 1 in which the controller is programmed to determine the amount of infusion fluid infused and the amount of urine output by weight.

6. The system of claim 1 in which the controller is programmed to calculate the amount of infusion fluid infused over a time interval and to calculate the amount of urine output over a time interval.

7. The system of claim 1 in which the controller is further configured to display on the console a net fluid gain or loss.

8. The system of claim 1 in which the controller is configured, based on the input set desired fluid balance, to administer a volume of infusion fluid equal to, less than, or greater than the volume of urine output by the patient.

9. The system of claim 1 in which the pump infuses fluid into the patient from a source of infusion fluid.

10. The system of claim 9 in which the infusion subsystem further includes a weighing mechanism for the source of infusion fluid and the controller is responsive to said weighing mechanism for determining the amount of infusion fluid infused into the patient.

11. The system of claim 10 in which the controller is further configured to monitor the operation of the pump and to calculate the amount of infusion fluid infused into the patient based on the monitored operation of the pump.

12. The system of claim 11 in which the controller is further configured to output a signal if the determined amount of infusion fluid infused into the patient based on the weight of the source of infused fluid differs from the calculated amount of fluid infused into the patient based on the monitored operation of the pump by a predetermined amount over a predetermined time period.

13. The system of claim 1 in which the controller is configured to determine a rate of change of urine output, calculate a desired infusion rate based on the determined rate of change of urine output and the desired fluid balance, and to adjust the operation of the infusion subsystem based on the calculated desired infusion rate.

14. The system of claim 1 in which the infusion subsystem further includes a pressure sensor configured to detect occlusion in the infusion subsystem.

15. The system of claim 14 in which the controller is responsive to the pressure sensor and configured to interrupt the balancing function in response to a detected pressure greater than a predetermined pressure.

16. The system of claim 15 in which the controller is further configured to resume the balancing function if the detected pressure reduces to a pressure below the predetermined pressure.

17. The system of claim 1 in which the console further includes a bolus input for setting a desired bolus amount of the said infusion fluid and the controller is further configured to control the infusion subsystem to administer the desired bolus amount of said infusion fluid in addition to the desired fluid balance.

18. The system of claim 1 in which the console further includes an input for setting a desired therapy time and the controller is configured to control the infusion subsystem to administer infusion fluid infused into the patient to balance the urine output with the infusion fluid based on an input desired fluid balance and an input desired therapy time.

19. The system of claim 1 in which the controller is further configured to determine one or more abnormal readings output by the infusion subsystem and/or the urine output measurement subsystem including readings indicating a lesser amount of urine than a previous reading, a greater amount of infusion fluid than a previous reading, and a sharply varying urine output reading or infusion fluid infused reading and, in response to a detected abnormal reading, control the infusion subsystem according to a predetermined function.

20. The system of claim 19 in which a predetermined function controls the infusion subsystem to infuse infusion fluid at a preset minimum infusion rate until the detected abnormal reading is no longer present or which controls the infusion subsystem to infuse infusion fluid at a rate established prior to detection of the abnormal reading.

21. A patient hydration system comprising:
an infusion subsystem including a pump which infuses an infusion fluid into a patient via infusion tubing connected to the patient in a balancing configuration;
a urine output measurement subsystem which measures urine output by the patient and including a urine collection chamber for collecting the urine output by the patient and connected to the patient via urine collection tubing in the balancing configuration;
a console including an input for setting a desired fluid balance, the console further including a priming input;
a priming adapter configured to connect the infusion tubing to the urine collection tubing in a priming configuration;
a controller configured, in response to the priming input and in the priming configuration, to automatically control the pump to drive infusion fluid through the infusion tubing, through the priming adapter and the urine collection tubing, and into the urine collection chamber; and
the controller configured, in response to the set desired fluid balance and in the balancing configuration, to automatically control the infusion subsystem to administer infusion fluid into the patient based on the set desired fluid balance and the amount of urine output by the patient, wherein the amount of urine output includes the amount of infusion fluid present in the urine collection tubing following the priming step which is driven into the urine collection chamber once the patient begins to expel urine.

22. A patient hydration method comprising:
connecting an infusion subsystem including infusion tubing to urine collection tubing connected to a urine collection chamber;
priming including driving infusion fluid through the infusion tubing, the urine collection tubing, and into the urine collection chamber;
disconnecting the infusion tubing from the urine collection tubing;
connecting the infusion tubing to the patient;
connecting the urine collection tubing to the patient;
determining the amount of urine output by the patient, wherein the amount of urine output includes the amount of infusion fluid present in the urine collection tubing following the priming step which is driven into the urine collection chamber once the patient begins to expel urine; and
automatically infusing fluid into the patient as a function of the determined amount of urine output by the patient and a desired fluid balance.

\* \* \* \* \*